(12) United States Patent
Humbarger et al.

(10) Patent No.: US 10,316,047 B2
(45) Date of Patent: Jun. 11, 2019

(54) PROCESSES FOR FORMING COORDINATION COMPLEXES CONTAINING MONOSULFONATED CATECHOLATE LIGANDS

(71) Applicant: Lockheed Martin Energy, LLC, Bethesda, MD (US)

(72) Inventors: Scott Thomas Humbarger, Cambridge, MA (US); Matthew Millard, Cambridge, MA (US)

(73) Assignee: Lockheed Martin Energy, LLC, Bethesda, MD (US)

( * ) Notice: Subject to any disclaimer, the term of this patent is extended or adjusted under 35 U.S.C. 154(b) by 606 days.

(21) Appl. No.: 15/060,495

(22) Filed: Mar. 3, 2016

(65) Prior Publication Data

US 2017/0253620 A1 Sep. 7, 2017

(51) Int. Cl.
*C07F 7/28* (2006.01)
*C07C 37/00* (2006.01)
(Continued)

(52) U.S. Cl.
CPC .............. *C07F 7/28* (2013.01); *C07C 303/06* (2013.01); *H01B 1/121* (2013.01); *H01M 8/08* (2013.01);
(Continued)

(58) Field of Classification Search
CPC ........... H01B 1/121; C07F 7/28; C07C 37/00; C07C 37/64
See application file for complete search history.

(56) References Cited

U.S. PATENT DOCUMENTS

| 1,279,295 A | 9/1918 | Downs |
| 1,988,575 A | 1/1935 | Schmidt |
(Continued)

FOREIGN PATENT DOCUMENTS

| CN | 1284208 A | 2/2001 |
| CN | 101877412 A | 11/2010 |
(Continued)

OTHER PUBLICATIONS

Murkami et al "The chelating behavior of catechol-4-sulfonate with iron(III) ion", Bulletin of the Chemical Society of Japan. vol. 36, No. 11, 1963. (Year: 1963).*

(Continued)

*Primary Examiner* — Mark Kopec
(74) *Attorney, Agent, or Firm* — BakerHostetler

(57) ABSTRACT

Coordination complexes can have a metal center with at least one unsubstituted catecholate ligand and at least one monosulfonated catecholate ligand or a salt thereof bound thereto. Some coordination complexes can have a formula of $D_gTi(L_1)_x(L_2)_y$, in which D is a counterion selected from $NH_4^+$, $Li^+$, $Na^+$, $K^+$, or any combination thereof; g ranges between 2 and 6; $L_1$ is an unsubstituted catecholate ligand; $L_2$ is a monosulfonated catecholate ligand; and x and y are non-zero numbers such that x+y=3. Methods for synthesizing such coordination complexes can include providing a neat mixture of catechol and a sub-stoichiometric amount of sulfuric acid, heating the neat mixture to form a reaction product containing catechol and a monosulfonated catechol or a salt thereof, and forming a coordination complex from the reaction product without separating the catechol and the monosulfonated catechol or the salt thereof from one another.

22 Claims, 5 Drawing Sheets

(51) Int. Cl.
*H01B 1/00* (2006.01)
*C07C 303/06* (2006.01)
*H01M 8/18* (2006.01)
*H01M 8/08* (2016.01)
*H01M 8/22* (2006.01)
*H01B 1/12* (2006.01)

(52) U.S. Cl.
CPC ........... *H01M 8/188* (2013.01); *H01M 8/222* (2013.01); *Y02E 60/528* (2013.01)

(56) References Cited

U.S. PATENT DOCUMENTS

| | | | |
|---|---|---|---|
| 2,353,782 A | 7/1944 | Neumark | |
| 2,415,792 A | 2/1947 | Gravell | |
| 3,294,588 A | 12/1966 | Morton | |
| 3,425,796 A | 2/1969 | Bauer | |
| 3,428,654 A | 2/1969 | Rubinfeld | |
| 3,573,984 A | 4/1971 | Shah | |
| 3,707,449 A | 12/1972 | Reinhardt et al. | |
| 3,772,379 A | 11/1973 | Woodgate | |
| 3,801,642 A | 4/1974 | Worrel | |
| 3,876,435 A | 4/1975 | Dollman | |
| 3,916,004 A | 10/1975 | Okada et al. | |
| 3,919,000 A | 11/1975 | Yarrington | |
| 3,920,756 A | 11/1975 | Tahara et al. | |
| 3,929,506 A | 12/1975 | Leddy et al. | |
| 3,985,517 A | 10/1976 | Johnson | |
| 3,985,585 A | 10/1976 | Tuttle et al. | |
| 4,009,212 A * | 2/1977 | Leston | C07C 37/04 568/766 |
| 4,046,861 A | 9/1977 | Reinhardt et al. | |
| 4,064,324 A | 12/1977 | Eustace | |
| 4,069,371 A | 1/1978 | Zito | |
| 4,115,648 A * | 9/1978 | Esteve-Subirana | C07C 309/00 544/110 |
| 4,126,529 A | 11/1978 | DeBerry | |
| 4,180,623 A | 12/1979 | Adams | |
| 4,202,799 A | 5/1980 | Yoshimura et al. | |
| 4,233,144 A | 11/1980 | Pace et al. | |
| 4,362,791 A | 12/1982 | Kaneko et al. | |
| 4,378,995 A | 4/1983 | Gratzfeld et al. | |
| 4,410,606 A | 10/1983 | Loutfy et al. | |
| 4,436,711 A | 3/1984 | Olson | |
| 4,436,712 A | 3/1984 | Olson | |
| 4,436,713 A | 3/1984 | Olson | |
| 4,436,714 A | 3/1984 | Olson | |
| 4,443,423 A | 4/1984 | Olson | |
| 4,443,424 A | 4/1984 | Olson | |
| 4,468,441 A | 8/1984 | D'Agostino et al. | |
| 4,485,154 A | 11/1984 | Remick et al. | |
| 4,520,083 A | 5/1985 | Prater et al. | |
| 4,563,403 A | 1/1986 | Julian | |
| 4,592,973 A | 6/1986 | Pemsler et al. | |
| 4,617,244 A | 10/1986 | Greene | |
| 4,680,308 A | 7/1987 | Schwartz et al. | |
| 4,818,646 A | 4/1989 | Takakubo et al. | |
| 4,880,758 A | 11/1989 | Heistand, II et al. | |
| 4,952,289 A | 8/1990 | Ciccone et al. | |
| 4,959,135 A | 9/1990 | Zenner et al. | |
| 4,973,720 A | 11/1990 | Saito et al. | |
| 5,084,533 A | 1/1992 | Shah et al. | |
| 5,102,906 A | 4/1992 | Nakayama et al. | |
| 5,122,461 A | 6/1992 | Hsiung et al. | |
| 5,264,097 A | 11/1993 | Vaughan | |
| 5,302,481 A | 4/1994 | Ong | |
| 5,318,865 A | 6/1994 | Kaneko et al. | |
| 5,433,934 A | 7/1995 | Chang et al. | |
| 5,472,807 A | 12/1995 | Licht et al. | |
| 5,643,670 A | 7/1997 | Chung | |
| 5,679,239 A | 10/1997 | Blum et al. | |
| 5,759,711 A | 6/1998 | Miyabayashi et al. | |
| 5,785,841 A | 7/1998 | Tseng | |
| 5,876,581 A | 3/1999 | Itaya et al. | |
| 5,910,366 A | 6/1999 | Chowdhury et al. | |
| 6,001,326 A | 12/1999 | Kim et al. | |
| 6,030,517 A | 2/2000 | Lincot et al. | |
| 6,054,230 A | 4/2000 | Kato | |
| 6,461,772 B1 | 10/2002 | Miyake et al. | |
| 6,475,661 B1 | 11/2002 | Pellegri et al. | |
| 6,485,868 B1 | 11/2002 | Tsujioka et al. | |
| 6,555,989 B1 | 4/2003 | Pearson | |
| 6,585,951 B1 | 7/2003 | Hong et al. | |
| 6,624,328 B1 | 9/2003 | Guerra | |
| 7,046,418 B2 | 5/2006 | Lin et al. | |
| 7,193,764 B2 | 3/2007 | Lin et al. | |
| 7,223,833 B1 | 5/2007 | Nielsen et al. | |
| 7,252,905 B2 | 8/2007 | Clarke et al. | |
| 7,265,162 B2 | 9/2007 | Yandrasits et al. | |
| 7,348,088 B2 | 3/2008 | Hamrock et al. | |
| 7,463,917 B2 | 12/2008 | Martinez | |
| 7,508,568 B2 | 3/2009 | Lin et al. | |
| 7,550,231 B2 | 6/2009 | Stauffer | |
| 7,557,164 B2 | 7/2009 | Felix et al. | |
| 7,625,663 B2 | 12/2009 | Clarke et al. | |
| 7,645,540 B2 | 1/2010 | Boone et al. | |
| 7,678,728 B2 | 3/2010 | Olson et al. | |
| 7,745,056 B2 | 6/2010 | Lee et al. | |
| 7,767,777 B2 | 8/2010 | Buesing et al. | |
| 7,927,731 B2 | 4/2011 | Sahu | |
| 7,931,981 B2 | 4/2011 | Boone et al. | |
| 7,935,366 B2 | 5/2011 | Pahuja et al. | |
| 7,998,335 B2 | 8/2011 | Feeney et al. | |
| 8,129,554 B2 | 3/2012 | Schwaiger | |
| 8,187,441 B2 | 5/2012 | Evans et al. | |
| 8,445,118 B2 | 5/2013 | Cordonier et al. | |
| 8,492,581 B2 * | 7/2013 | Frost | C07C 303/06 562/45 |
| 8,691,413 B2 | 4/2014 | Esswein et al. | |
| 8,753,761 B2 | 6/2014 | Esswein et al. | |
| 9,300,000 B2 | 3/2016 | Jansen et al. | |
| 9,382,274 B2 | 7/2016 | Esswein et al. | |
| 9,409,842 B1 | 8/2016 | Fu et al. | |
| 2002/0177042 A1 | 11/2002 | Amendola | |
| 2003/0068561 A1 | 4/2003 | Okahara et al. | |
| 2003/0143456 A1 | 7/2003 | Kazacos et al. | |
| 2003/0228394 A1 | 12/2003 | Abdel-Monem et al. | |
| 2004/0096746 A1 | 5/2004 | Wietelmann et al. | |
| 2005/0098437 A1 | 5/2005 | Shiepe | |
| 2005/0244707 A1 | 11/2005 | Skyllas-Kazacos et al. | |
| 2006/0047094 A1 | 3/2006 | Cherkasov et al. | |
| 2007/0275291 A1 | 11/2007 | Gu et al. | |
| 2008/0274385 A1 | 11/2008 | Creeth | |
| 2008/0292964 A1 | 11/2008 | Kazacos et al. | |
| 2009/0110998 A1 | 4/2009 | Miyachi et al. | |
| 2009/0130525 A1 | 5/2009 | Miyachi et al. | |
| 2009/0208807 A1 | 8/2009 | Miyachi et al. | |
| 2009/0308752 A1 | 12/2009 | Evans et al. | |
| 2010/0003586 A1 | 1/2010 | Sahu | |
| 2010/0059388 A1 | 3/2010 | Clarke et al. | |
| 2010/0086823 A1 | 4/2010 | Koshino et al. | |
| 2010/0086983 A1 | 4/2010 | Gellett et al. | |
| 2010/0239946 A1 | 9/2010 | Miyachi et al. | |
| 2011/0014532 A1 | 1/2011 | Knuckey et al. | |
| 2011/0136016 A1 | 6/2011 | Huang et al. | |
| 2011/0189549 A1 | 8/2011 | Sun et al. | |
| 2011/0195283 A1 | 8/2011 | Sun et al. | |
| 2011/0200890 A1 | 8/2011 | Kocherginsky | |
| 2011/0223450 A1 | 9/2011 | Horne et al. | |
| 2011/0244277 A1 | 10/2011 | Gordon, II et al. | |
| 2011/0244367 A1 | 10/2011 | Watahiki et al. | |
| 2012/0052347 A1 | 3/2012 | Wilson et al. | |
| 2012/0077095 A1 | 3/2012 | Roumi et al. | |
| 2012/0107661 A1 | 5/2012 | Lee et al. | |
| 2012/0135278 A1 | 5/2012 | Yoshie et al. | |
| 2012/0171541 A1 | 7/2012 | Park et al. | |
| 2012/0183868 A1 | 7/2012 | Toussaint et al. | |
| 2012/0196188 A1 | 8/2012 | Zhang et al. | |
| 2012/0202099 A1 | 8/2012 | Perry et al. | |
| 2012/0208061 A1 | 8/2012 | Sahu et al. | |
| 2012/0244406 A1 | 9/2012 | Xia et al. | |
| 2012/0263990 A1 | 10/2012 | Kim | |
| 2013/0004819 A1 | 1/2013 | Mun et al. | |

(56) References Cited

U.S. PATENT DOCUMENTS

| | | | |
|---|---|---|---|
| 2013/0157087 A1 | 6/2013 | Pandy et al. | |
| 2013/0252062 A1 | 9/2013 | Wilkins et al. | |
| 2013/0252137 A1 | 9/2013 | Zhang et al. | |
| 2014/0028260 A1 | 1/2014 | Goeltz et al. | |
| 2014/0028261 A1 | 1/2014 | Esswein et al. | |
| 2014/0030572 A1 | 1/2014 | Esswein et al. | |
| 2014/0030573 A1 | 1/2014 | Esswein et al. | |
| 2014/0030631 A1 | 1/2014 | Esswein et al. | |
| 2014/0051002 A1 | 2/2014 | Esswein et al. | |
| 2014/0051003 A1 | 2/2014 | Esswein et al. | |
| 2014/0080035 A1 | 3/2014 | Esswein et al. | |
| 2014/0138576 A1 | 5/2014 | Esswein et al. | |
| 2014/0178735 A1 | 6/2014 | Wang et al. | |
| 2014/0193687 A1 | 7/2014 | Park et al. | |
| 2014/0239906 A1 | 8/2014 | Anderson et al. | |
| 2014/0274936 A1 | 9/2014 | Piccariello et al. | |
| 2014/0349177 A1 | 11/2014 | Chung et al. | |
| 2014/0370403 A1 | 12/2014 | Narayan et al. | |
| 2014/0377666 A1 | 12/2014 | Kodama et al. | |
| 2015/0236543 A1 | 8/2015 | Brushett et al. | |
| 2015/0372333 A1 | 12/2015 | Odom et al. | |
| 2016/0066578 A1 | 3/2016 | Ala'Aldeen et al. | |
| 2016/0149251 A1 | 5/2016 | Reece | |
| 2016/0208165 A1 | 7/2016 | Li et al. | |
| 2016/0264603 A1 | 9/2016 | Esswein et al. | |
| 2016/0268623 A1 | 9/2016 | Esswein et al. | |
| 2016/0272659 A1 | 9/2016 | King et al. | |
| 2016/0276693 A1 | 9/2016 | Goeltz et al. | |
| 2016/0276694 A1 | 9/2016 | Goeltz et al. | |
| 2016/0276695 A1 | 9/2016 | Esswein et al. | |
| 2017/0256811 A1* | 9/2017 | Humbarger | C07F 7/28 |
| 2017/0271704 A1 | 9/2017 | Morris-Cohen | |
| 2018/0029965 A1 | 2/2018 | Millard | |
| 2018/0029966 A1 | 2/2018 | Millard et al. | |
| 2018/0105544 A1 | 4/2018 | Humbarger et al. | |
| 2018/0233762 A1* | 8/2018 | Millard | H01M 8/188 |

FOREIGN PATENT DOCUMENTS

| | | |
|---|---|---|
| EP | 0814527 A2 | 12/1997 |
| EP | 1290068 A2 | 3/2003 |
| EP | 1411576 A1 | 4/2004 |
| EP | 1901379 A1 | 3/2008 |
| EP | 2235781 A1 | 10/2010 |
| EP | 2463950 A1 | 6/2012 |
| FR | 1533662 A | 7/1968 |
| GB | 1354886 A | 6/1974 |
| WO | WO-95/12219 A1 | 5/1995 |
| WO | WO-1997/017354 A1 | 5/1997 |
| WO | WO-00/56302 A1 | 9/2000 |
| WO | WO-2004/095602 A2 | 11/2004 |
| WO | WO-2006/135958 A1 | 12/2006 |
| WO | WO-2007/044852 A2 | 4/2007 |
| WO | WO-2007/101284 A1 | 9/2007 |
| WO | WO-2011/075135 A1 | 6/2011 |
| WO | WO-2011/098781 A1 | 8/2011 |
| WO | WO-2011/149624 A1 | 12/2011 |
| WO | WO-2012/075810 A1 | 6/2012 |
| WO | WO-2013/006427 A1 | 1/2013 |
| WO | WO-2013/048603 A1 | 4/2013 |
| WO | WO-2014/052682 A2 | 4/2014 |
| WO | WO-2015/069439 A1 | 5/2015 |

OTHER PUBLICATIONS

Murkami et al "Stability order in metal chelate compounds. I. 4-carboxy- and 4-sulfocatechol complexes", Bulletin of the Chemical Society of Japan. vol. 36, No. 06, 1963. (Year: 1963).*

Ahluwalia et al., Intermediates for Organic Synthesis, Chapter 1, Phenols, Sections 1.21 and 1.23, (2003), I.K. International Pvt. Ltd.

Extended European Search Report from European Patent Application No. 15863021, dated May 17, 2018, 11 pages.

Chi et al., "Structural characterization of Sr—Ti and Ba—Ti catecholate complexes: single source precursors fro SrTiO3 and BaTiO3 binary oxides," Journal of Physics and Chemistry of Solids, 2001, vol. 62, pp. 1871-1879.

Ali et al., "Synthesis and Processing Characteristics of $Ba_{0.65}Sr_{0.35}TiO_3$ Powders from Catecholate Precursors," J Am Ceram Soc, 1993, pp. 2321-2326, vol. 76, No. 9.

Devi et al., "pH-metric investigation on Mixed-Ligand Complexes of Ca(II), Mg(II) and Zn(II) with L-Dopa and 1,10 Phenantroline in Propylene glycol-Water Mixtures," RRJC, Oct.-Dec. 2012, vol. 1, Issue 1, pp. 13-22.

Xu, "Mechanics of metal-catecholate complexes: The roles of coordination state and metal types," Scientific Reports, Oct. 10, 2013, 3:2914, pp. 1-7.

Soloveichik, "Flow Batteries: Current Status and Trends," 2015, Chem. Rev., 115 (20), pp. 11533-11558.

Davies, "Electroceramics from Source Materials via Molecular Intermediates: $BaTIO_3$ from $TIO_2$ via $[TI(catecholate)_3]^{2-}$," May 1990, J. Am. Ceram. Soc., Aug. 1990, 73(5), 1429-30.

Ahn et al., "A Study of Benzene 1,2,4-Trisphosphate Derivatives as Inositol 1,4,5-Trisphosphate 3-Kinase Inhibitors," Bull. Korean Chem. Soc., 2002, pp. 515-517, vol. 23., No. 3.

Bosch et al., "Novel Catalysis of Hydroquinone Autoxidation with Nitrogen Oxides," J. Org. Chem., 1994, pp. 2529-2536, 59.

Lang et al., "Studies on the Biosynthesis of Bovilactone-4,4 and Related Fungal Meroterpenoids," Eur. J. Org. Chem., 2008, pp. 3544-3551.

Lang et al., "Studies on the Structure and Biosynthesis of Tridentoquinone and Related Meroterpenoids from the Mushroom Suillus tridentinus (Boletales)," Eur. J. Org. Chem., 2008, pp. 816-825.

Mcomie et al. "The Thiele-Winter Acetoxylation of Quinones," Organic Reactions, 1972, pp. 199-277, 19, John Wiley and Sons, Inc., New York.

Spyroudis, "Hydroxyquinones: Synthesis and Reactivity," Molecules, 2000, pp. 1291-1330, 5.

H. Cerofontain, et al., "Sulfonation and sulfation on reaction of 1,2-dihydroxybenzene and its methyl ethers in concentrated aqueous sulfuric acid," Recl. Trav. Chim. Pays-Bas., 1988, pp. 325-330, 107.

S. Saito, et al. "DPPH radical-scavenging reaction of protocatechuic acid: difference in reactivity between adds and their esters," Helv. Chim. Acta, 2006, pp. 1395-1407, 89.

International Search Report and Written Opinion from PCT/US17/43393, dated Oct. 5, 2017, 7 pages.

W. Maison, et al., "Effect of Calcination Temperature on Phase Transformation and Particle size of Barium Titanate Fine Powders Synthesized by the Catecholate Process," ScienceAsia, 2001, pp. 239-243, 27.

Vliet et al., "Hydroxyhydroquinone Triacetate," Organic Synthesys, 1941, Coll vol. 1, p. 317 (1941), vol. 4, p. 35 (1925) 3 pages.

International Search Report and Written Opinion dated Jan. 19, 2017 from International Application No. PCT/US16/58433.

International Search Report and Written Opinion dated Feb. 17, 2017 from International Application No. PCT/US16/65159.

Borgias, et al., "Synthetic, Structural, and Physical Studies of Titanium Complexes of Catechol and 3,5-Di-tert-butylcatechol," Inorganic Chemistry, 194, vol. 23, No. 8, 1009-1016.

Sever, et al., "Visible absorption spectra of metal-catecholate and metal-tironate complexes," Dalton Transations, 2004, vol. 7, pp. 1061-1072.

Abdulghani et al., "Preparation and Characterization of Di-, Tri-, and Tetranuclear Schiff Base Complexes Derived from Diamines and 3,4-Dihydroxybenzaldehyde," Hindawi Publishing Corp, Bioinorganic Chemistry and Applications, 2013, pp. 1-14.

IUPAC Compendium of Chemical Terminology, "coordinatively unsaturated complex," 1997, http://old.iupac.org/goldbook/C01334.pdf.

Mansoor, "Mixed Metal Complexes of Copper (II), Nickel (II) and Zinc (II) Involving Dopa and Dopamine," International Journal of ChemTech Research, Jan.-Mar. 2010, vol. 2, No. 1, pp. 640-645.

International Search Report and Written Opinion from PCT/US17/14764, dated Apr. 20, 2017.

(56) References Cited

OTHER PUBLICATIONS

International Search Report and Written Opinion from PCT/US16/69190, dated May 3, 2017.
International Search Report and Written Opinion from PCT/US2017/022203, dated Jun. 6, 2017.
Wang et al., "Issues in Freeze Drying of Aqueous Solutions," Chinese Journal of Chemical Engineering, 2012, 20(3), pp. 551-559.
Brezina, "Study of the reduction of oxygen on a carbon paste electrode in an alkaline medium," Coll. Czech. Chem. Commun., 1973, 38(10), 3024-3031.
Caulton, "Systematics and Future Projections Concerning Redox-Noninnocent Amide/Imine Ligands," Eur. J. Inorg. Chem., Jan. 2012, 2012(3), 435-443.
Chen, "Solution Redox Couples for Electrochemical Energy Storage: I. Iron (III)-Iron (II) Complexes with O-Phenanthroline and Related Ligands," Journal of the Electrochemical Society, Jul. 1981, 128(7), 1460-1467.
Cohen, "The Association of Ferrocyanide Ions With Various Cations," J. Phys. Chem., Aug. 1957, 61(8), 1096-1100.
Davies, "Electroceramics from Source Materials via Molecular Intermediates: PbTi03 from Ti02 via [Ti(catecholate)3]2-," J. Am. Ceram. Soc., Aug. 1990, 73(8), 2570-2572.
Dehaen et al, "A Self-Assembled Complex with a Titanium (IV) Catecholate Core as a Potential Bimodal Contrast Agent," Chem Eur J, 2012, pp. 293-302, vol. 18.
Fryda, "Wastewater Treatment With Diamond Electrodes," Diamond Materials, Electrochemical Society Proceedings, 2000, 99(32), 473-483.
Gail, "Cyano Compounds, Inorganic" in Ullmann's Encyclopedia of Industrial Chemistry, 2012, 10, 674-710.
Hollandsworth, "Zinc/Ferrocyanide Battery Development Phase IV" Lockheed Missiles and Space Company, Inc., Contractor report, Sandia Contract DE-AC04-76DP00789, May 1985, 278 pages.
Kim, "Novel catalytic effects of Mn304 for all vanadium redox flow batteries," Chem. Commun., Apr. 2012, 48(44), 5455-5457.
Kulesza, "Electrochemical preparation and characterization of hybrid films composed of Prussian blue type metal hexacyanoferrate and conducting polymer," Electrochimica Acta, Aug. 2001, 46(26-27), 4065-4073.
Leung, "Development of a Zinc—Cerium Redox Flow Battery", 2011, 352 pages.
Leung, "An undivided zinc—cerium redox flow battery operating at room temperature (295 K)," Electrochemistry Communications, 2011, vol. 13, pp. 770-773.
Leung, "Ce(III)/Ce(iV) in methanesulfonic acid as the positive half cell of a redox flow battery," Electrochimica Acta, 2011, vol. 56, pp. 2145-2153.
Leung, "Zinc deposition and dissolution in methanesulfonic acid onto a carbon composite electrode as the negative electrode reactions in a hybrid redox flow battery," Electrochimica Acta, 2011, vol. 56, pp. 6536-6546.
Leung, "Characterization of a zinc—cerium flow battery," Journal of Power Sources, 2011, vol. 195, pp. 5174-5185.
Modiba, "Electrochemical impedance spectroscopy study of Ce(IV) with aminopolycarboxylate ligands for redox flow batteries applications," Journal of Power Sources, May 2012, vol. 205, 1-9.
Modiba, "Electrochemical study of cerium(IV) in the presence of ethylenediaminetetraacetic acid (EDTA) and diethylenetriaminepentaacetate (DTPA) ligands," Journal of Applied Electrochemistry, Sep. 2008, 38(9), 1293-1299.
Modiba, "Electrolytes for redox flow battery systems," Dissertation presented for the degree of Doctor of Philosophy Chemistry at the University of Stellenbosch, Department of Chemistry and Polymer Science, Mar. 2010.
Nguyen, "Flow Batteries," The Electrochemical Society Interface, Fall2010, 19(3), 54-56.
Pharr, "Infrared Spectroelectrochemical Analysis of Adsorbed Hexacyanoferrate Species Formed during Potential Cycling in the Ferrocyanide/Ferricyanide Redox Couple," Anal. Chem., Nov. 1997, 69(22), 4673-4679.
Raymond , "Coordination isomers of biological iron transport compounds. VI. Models of the enterobactin coordination site. A crystal field effect in the structure of potassium tris( catecholato)chromate( III) and -ferrate( III) sesq u ihyd rates, $K_3[M(O_2C_6H_4)_3] \cdot 1.5H_2O$, M=chromium, iron," J. Am. Chem. Soc., Mar. 1976, 98(7), 1767-1774.
SIGMA-ALDRICH Tris(hydroxymethyl)aminomethane, 2015.
Sommer, "Titanium (IV) complexes with ligands having oxygen donor atoms in aqueous solutions," Zeitschrift fur Anorganische und Aligemeine Chemie, Mar. 1963, pp. 191-197, vol. 321, issue 3-4.
Steenken, "One-electron redox potentials of phenols. Hydroxy- and aminophenols and related compounds of biological interest," J. Phys. Chem., Sep. 1982, 86(18), 3661-3667.
Torres-Gomez, "Energy Storage in Hybrid Organic-Inorganic Materials Hexacyanoferrate-Doped Polypyrrole as Cathode in Reversible Lithium Cells," J. of the Electrochemical Society, 2000, 147(7), 2513-2516.
Trant, "Solubility of Sodium Ferrocyanide and Potassium Ferrocyanide in Solutions of NaOH and KOH Mixtures at 25.degree. C," University of Rochester, The David T. Kearns Center, Xerox Undergraduate Research Fellows Program, Jul. 28, 2011, 1 page.
Vercillo, "Solubility of Sodium Ferrocyanide in Sodium Hydroxide and Potassium Ferrocyanide in Potassium Hydroxide," University of Rochester, The David T. Kearns Center, Xerox Undergraduate Research Fellows Program, Jul. 28, 2011, 1 page.
Wang, "Determination of iron, titanium, osmium, and aluminum with tiron by reversephase high performance liquid chromatography/electrochemistry," Microchem. J., Jun. 1991, 43(3), 191-197.
Weber, "Redox flow batteries: a review," Journal of Applied Electrochemistry, Oct. 2011, 41(10), 1137-1164.
Murakami et al., "The Chelating Behavior of Catechol-4-sulfonate with Iron(III) Ion," Bulletin of the Chemical Society of Japan, 1963, pp. 1408-1411; vol. 36.
Westervelt, "A Study of the Calcium Complex of the Potassium Salt of Catechol-4-Sulfonate in Aqueous, Alkalino Media," Jan. 1981, Doctoral Dissertation, retrieved from https://smartech.gatech.edu/bitstream/handle/1853/5723/westervelt-iii_hh.pdf.

\* cited by examiner

PROCESSES FOR FORMING COORDINATION COMPLEXES CONTAINING MONOSULFONATED CATECHOLATE LIGANDS

CROSS-REFERENCE TO RELATED APPLICATIONS

Not applicable.

STATEMENT REGARDING FEDERALLY SPONSORED RESEARCH OR DEVELOPMENT

Not applicable.

FIELD

The present disclosure generally relates to coordination complexes and flow batteries containing coordination complexes as active materials and, more specifically, to methods for preparing coordination complexes having a mixture of ligands.

BACKGROUND

Electrochemical energy storage systems, such as batteries, supercapacitors and the like, have been widely proposed for large-scale energy storage applications. Various battery designs, including flow batteries, have been considered for this purpose. Compared to other types of electrochemical energy storage systems, flow batteries can be advantageous, particularly for large-scale applications, due to their ability to decouple the parameters of power density and energy density from one another.

Flow batteries generally include negative and positive active materials in corresponding electrolyte solutions, which are flowed separately across opposing sides of a membrane or separator in an electrochemical cell containing negative and positive electrodes. The flow battery is charged or discharged through electrochemical reactions of the active materials that occur inside the two half-cells. As used herein, the terms "active material," "electroactive material," "redox-active material" or variants thereof will synonymously refer to materials that undergo a change in oxidation state during operation of a flow battery or like electrochemical energy storage system (i.e., during charging or discharging). Although flow batteries hold significant promise for large-scale energy storage applications, they have often been plagued by sub-optimal energy storage performance (e.g., round trip energy efficiency) and limited cycle life, among other factors. Despite significant investigational efforts, no commercially viable flow battery technologies have yet been developed.

Metal-based active materials can often be desirable for use in flow batteries and other electrochemical energy storage systems. Although non-ligated metal ions (e.g., dissolved salts of a redox-active metal) can be used as an active material, it can often be more desirable to utilize coordination complexes for this purpose. As used herein, the terms "coordination complex, "coordination compound," and "metal-ligand complex" will synonymously refer to a compound having at least one covalent bond formed between a metal center and a donor ligand. The metal center can cycle between an oxidized form and a reduced form in an electrolyte solution, where the oxidized and reduced forms of the metal center represent states of full charge or full discharge depending upon the particular half-cell in which the coordination complex is present.

A difficulty with coordination complexes, particularly those containing organic ligands, is that they often can have relatively poor solubility characteristics as a result of ligand hydrophobicity, particularly in aqueous media. Other factors such as packing and van der Waals interaction can also impact solubility characteristics. Poor solubility can result in sub-optimal performance of a flow battery due to the need to maintain a low concentration of active material in an electrolyte solution. Moreover, poor solubility of an active material can result in potentially damaging precipitation within the various components of a flow battery system. For example, precipitation can occlude various flow pathways, foul membranes, and/or damage pumps within a flow battery system. Maintaining an electrolyte solution near an active material's saturation concentration to achieve good electrochemical performance can be especially precarious due to these types of precipitation concerns.

In view of the foregoing, active materials based upon high-solubility coordination complexes and facile methods for producing such coordination complexes would be highly desirable in the art. The present disclosure satisfies the foregoing needs and provides related advantages as well.

SUMMARY

In some embodiments, methods for synthesizing coordination complexes can include providing a neat mixture of catechol and a sub-stoichiometric amount of sulfuric acid relative to the catechol, heating the neat mixture to form a reaction product containing a mixture of catechol and a monosulfonated catechol or a salt thereof, and without separating the catechol and the monosulfonated catechol or the salt thereof from one another, forming a coordination complex from the reaction product. The coordination complex has a metal center with at least one unsubstituted catecholate ligand and at least one monosulfonated catecholate ligand bound thereto.

In other various embodiments, methods for synthesizing coordination complexes can include providing a neat mixture of catechol and up to about 0.7 stoichiometric equivalents of sulfuric acid relative to the catechol; heating the neat mixture at a temperature of about 80° C. or above to form a reaction product containing a mixture of catechol and a monosulfonated catechol or a salt thereof; without separating the catechol and the monosulfonated catechol or the salt thereof from one another, forming a coordination complex from the reaction product; combining an aqueous base with the coordination complex; and obtaining an aqueous solution of the coordination complex. The coordination complex has a metal center with at least one unsubstituted catecholate ligand and at least one monosulfonated catecholate ligand bound thereto. The monosulfonated catechol is 3,4-dihydroxybenzenesulfonic acid.

In some embodiments, compositions of the present disclosure can include a coordination complex dissolved in an aqueous solution having an alkaline pH. The coordination complex has a metal center with at least one unsubstituted catecholate ligand and at least one monosulfonated catecholate ligand bound thereto. The at least one monosulfonated catecholate ligand is 3,4-dihydroxybenzenesulfonic acid. The coordination complex bears an overall negative charge and at least one positively charged monovalent counterion maintains charge balance.

In still other various embodiments, flow batteries containing compositions of the present disclosure are described herein. More specifically, flow batteries of the present disclosure can include a first half-cell having a first electrolyte solution therein, where the first electrolyte solution includes a composition of the present disclosure.

The foregoing has outlined rather broadly the features of the present disclosure in order that the detailed description that follows can be better understood. Additional features and advantages of the disclosure will be described hereinafter. These and other advantages and features will become more apparent from the following description.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
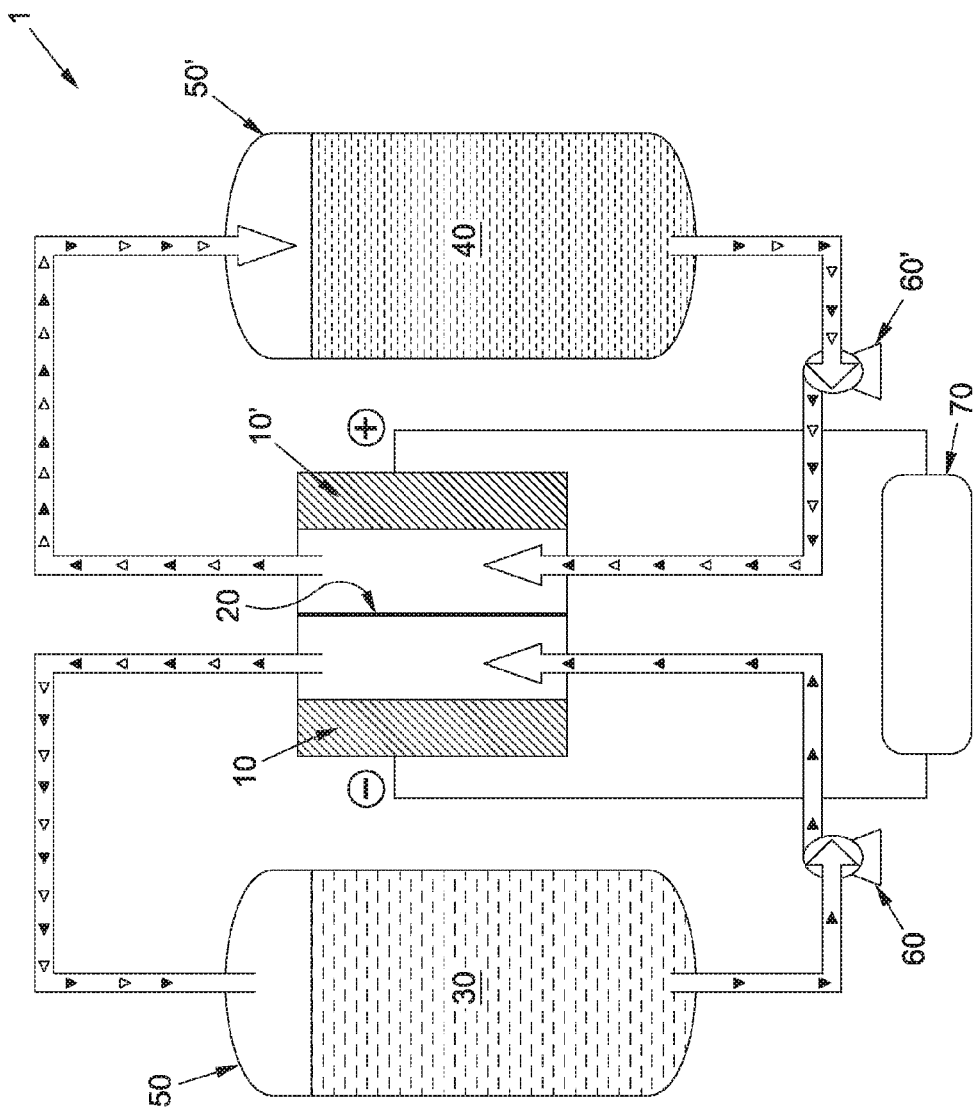
FIG. 1 shows a schematic of an illustrative flow battery.

The present disclosure is directed, in part, to flow batteries and compositions containing coordination complexes having at least one catecholate ligand and at least one monosulfonated catecholate ligand bound to a metal center. The present disclosure is also directed, in part, to methods for synthesizing monosulfonated catecholate ligands, specifically 3,4-dihydroxybenzenesulfonic acid (4-catecholsulfonic acid) or a salt thereof, and coordination complexes containing these ligands in combination with catecholate ligands.

More particularly, the present disclosure is directed, in part, to flow batteries and coordination complexes containing a mixture of at least one monosulfonated catecholate ligand, specifically 3,4-dihydroxybenzenesulfonic acid, and at least one catecholate ligand. The present disclosure is also directed, in part, to methods for synthesizing such coordination complexes from an as-synthesized mixture of catechol and monosulfonated catechol or a salt thereof.

The present disclosure may be understood more readily by reference to the following description taken in connection with the accompanying figures and examples, all of which form a part of this disclosure. It is to be understood that this disclosure is not limited to the specific products, methods, conditions or parameters described and/or shown herein. Further, the terminology used herein is for purposes of describing particular embodiments by way of example only and is not intended to be limiting unless otherwise specified. Similarly, unless specifically stated otherwise, any description herein directed to a composition is intended to refer to both solid and liquid versions of the composition, including solutions and electrolytes containing the composition, and electrochemical cells, flow batteries, and other energy storage systems containing such solutions and electrolytes. Further, it is to be recognized that where the disclosure herein describes an electrochemical cell, flow battery, or other energy storage system, it is to be appreciated that methods for operating the electrochemical cell, flow battery, or other energy storage system are also implicitly described.

It is also to be appreciated that certain features of the present disclosure may be described herein in the context of separate embodiments for clarity purposes, but may also be provided in combination with one another in a single embodiment. That is, unless obviously incompatible or specifically excluded, each individual embodiment is deemed to be combinable with any other embodiment(s) and the combination is considered to represent another distinct embodiment. Conversely, various features of the present disclosure that are described in the context of a single embodiment for brevity's sake may also be provided separately or in any sub-combination. Finally, while a particular embodiment may be described as part of a series of steps or part of a more general structure, each step or sub-structure may also be considered an independent embodiment in itself.

Unless stated otherwise, it is to be understood that each individual element in a list and every combination of individual elements in that list is to be interpreted as a distinct embodiment. For example, a list of embodiments presented as "A, B, or C" is to be interpreted as including the embodiments "A," "B," "C," "A or B," "A or C," "B or C," or "A, B, or C."

In the present disclosure, the singular forms of the articles "a," "an," and "the" also include the corresponding plural references, and reference to a particular numerical value includes at least that particular value, unless the context clearly indicates otherwise. Thus, for example, reference to "a material" is a reference to at least one of such materials and equivalents thereof.

In general, use of the term "about" indicates approximations that can vary depending on the desired properties sought to be obtained by the disclosed subject matter and is to be interpreted in a context-dependent manner based on functionality. Accordingly, one having ordinary skill in the art will be able to interpret a degree of variance on a case-by-case basis. In some instances, the number of significant figures used when expressing a particular value may be a representative technique of determining the variance permitted by the term "about." In other cases, the gradations in a series of values may be used to determine the range of variance permitted by the term "about." Further, all ranges in the present disclosure are inclusive and combinable, and references to values stated in ranges include every value within that range.

As discussed above, energy storage systems that are operable on a large scale while maintaining high efficiency values can be extremely desirable. Flow batteries have generated significant interest in this regard, but there remains considerable room for improving their operating characteristics. Although coordination complexes have been explored for use as active materials within flow batteries, the limited solubility of coordination complexes can sometimes be problematic, particularly for aqueous electrolyte solutions. In addition, high conductivity values can also sometimes be difficult to achieve. Exemplary description of illustrative flow batteries, their use, and operating characteristics is provided hereinbelow.

Coordination complexes containing at least one catecholate ligand can be particularly desirable active materials for use in flow batteries and other electrochemical systems. As used herein, the term "catechol" will refer to a compound having an aromatic ring bearing hydroxyl groups on adjacent carbon atoms (i.e., 1,2-hydroxyl groups). Optional substitution can also be present in addition to the 1,2-hydroxyl groups. As used herein, the term "catecholate" will refer to a substituted or unsubstituted catechol compound that is bound to a metal center via a metal-ligand bond. As used herein, the term "unsubstituted catecholate" will refer to the particular case where 1,2-dihydroxybenzene (catechol) is bound to a metal center via a metal-ligand bond. Like many other organic ligands, the relatively hydrophobic nature of common catecholate ligands and the resultant low solubility of their coordination complexes can be problematic for the reasons discussed above. Other factors can also lead to problematic solubility performance in some cases.

The present inventors recognized that the energy density and other operating parameters of flow batteries and related electrochemical systems could be improved by increasing the solubility of catecholate coordination complexes while maintaining their desirable electrochemical properties. To this end, the inventors discovered that monosulfonated catecholate ligands can improve the solubility of coordination complexes while maintaining desirable electrochemical properties that are at least comparable to those of coordination complexes containing non-sulfonated catecholate ligands, including unfunctionalized catecholate ligands. Titanium coordination complexes containing at least one monosulfonated catecholate ligand can be particularly desirable for this purpose. As used herein, the term "monosulfonated catecholate ligand" will refer to a substituted catecholate ligand bearing one sulfonic acid group or any salt thereof.

Although monosulfonated catecholate ligands can form coordination complexes having increased solubility and desirable electrochemical properties, the inventors surprisingly found that further sulfonic acid substitution on the catecholate aromatic ring can be problematic. For instance, in the case of titanium, the inventors found that titanium catecholate complexes containing at least one disulfonated catecholate ligand (e.g., 4,5-dihydroxy-1,3-benzenedisulfonic acid) were unstable under the operating conditions of a flow battery. In contrast, corresponding titanium coordination complexes containing at least one monosulfonated catecholate ligand remained stable under similar conditions.

Whereas 4,5-dihydroxy-1,3-benzenedisulfonic acid (trade name TIRON) is a disulfonated catecholate ligand that is commercially available, corresponding monosulfonated catecholate ligands having sulfonic acid substitution in either the 1- or the 3-position of the catechol aromatic ring are not commercially available. In fact, there is only scant mention of such compounds in the chemical literature, and the known processes for their synthesis are generally low-yielding, provide difficult-to-separate reaction mixtures, and/or, depending on conditions, result in non-regioselective reactivity at the 1- and the 3-positions of the aromatic ring. Certain reaction conditions can form side products that can be undesirable for incorporation in an electrolyte solution The present inventors also discovered a convenient and scalable synthetic method for producing monosulfonated catecholate ligands with a high degree of regioselectivity. In particular, the inventors discovered that by reacting a neat mixture of catechol and a near-equivalent to a sub-stoichiometric amount of sulfuric acid together with one another, predominantly monosulfonated catechol could be produced. By heating the neat mixture to a sufficiently high temperature, predominantly 3,4-dihydroxybenzenesulfonic acid can be formed. In contrast, at or near room temperature, otherwise similar reaction conditions form a reaction product also containing a significant fraction of 2,3-dihydroxybenzenesulfonic acid.

Although high conversion percentages of catechol to 3,4-dihydroxybenzenesulfonic acid can be realized by utilizing a near-stoichiometric amount of sulfuric acid, isolation and purification of the monosulfonated catechol can prove challenging due to this compound's exceedingly high aqueous solubility. For example, any disulfonated catecholate ligands that form under the reaction conditions can be difficult to separate from the desired monosulfonated catechol. Incorporation of even small amounts of disulfonated catecholate ligands into coordination complexes destined for use in a flow battery can be problematic for the reasons discussed in detail above.

The inventors additionally discovered that by further lowering the number of stoichiometric equivalents of sulfuric acid relative to catechol, the extent of disulfonated catecholate ligand formation could be significantly decreased. For example, the inventors found that minimal disulfonation occurred when utilizing only about 0.33 stoichiometric equivalents of sulfuric acid relative to catechol, in which case a reaction product containing a mixture of about 0.33 equivalents of 3,4-dihydroxybenzenesulfonic acid and about 0.67 equivalents of unreacted catechol was obtained. More generally, quantities of sulfuric acid up to about 0.7 stoichiometric equivalents relative to catechol can form substantially monosulfonated catechol compounds for the catechol that is converted into product. Even sub-stoichiometric amounts of sulfuric acid resulting in incorporation of less than one sulfonic acid group on average to a catechol ring can be useful in the various embodiments of the present disclosure. Like the near-stoichiometric reaction conditions discussed above, the unreacted catechol can be removed from the monosulfonated catechol formed under sub-stoichiometric conditions by performing an organic solvent wash to leave the monosulfonated catechol in an aqueous phase. However, this approach can be undesirable due to the inefficient use of the catechol starting material and costs associated with ensuing isolation, purification and waste disposal processes.

The inventors further recognized that the mixture of catechol and monosulfonated catechol produced under sub-stoichiometric reaction conditions could be used directly to form coordination complexes containing both unsubstituted catecholate ligands and sulfonated catecholate ligands or a salt thereof. Advantageously, both catechol and monosulfonated catechols can display similar reactivity toward forming coordination complexes with titanium and other metals. Hence, the synthesis and purification conditions for unsubstituted metal catecholate complexes can be readily adapted to the coordination complexes produced in accordance with the present disclosure. The synthetic approach of the present disclosure can also provide a number of other operational benefits and other advantages. Foremost, such techniques can eliminate the time and expense needed for isolating and purifying monosubstituted catechols. Moreover, techniques of the present disclosure can utilize unreacted catechol that would otherwise be directed to a waste stream or need re-purification for recycling. In addition, single-vessel (i.e., "one-pot") processes for sulfonating catechol and forming coordination complexes therefrom can be realized by applying the methods of the present disclosure.

Coordination complexes produced in accordance with the present disclosure can have both unsubstituted catecholate ligands and sulfonated catecholate ligands bound to the metal center. The combination of both unsubstituted catecholate ligands and sulfonated catecholate ligands bound to the same metal center can be desirable to limit the amount of negative-charged sulfonate anions that are present, such the coordination complexes that would be produced through reacting only the sulfonated catechol with a metal compound. Whereas one or two sulfonate anions can desirably improve solubility and maintain desirable operating properties in an electrochemical system, incorporating a third sulfonate anion can be problematic in some instances due to excessive viscosification effects. Effectively, the unsubstituted catecholate ligand can "dilute" the amount of charge that is introduced within the coordination complexes.

As a further advantage, coordination complexes produced in accordance with the present disclosure can be readily isolated within an aqueous alkaline solution due to the solubility-promoting effects of the sulfonic acid group(s). Specifically, upon forming the coordination complex, the reaction mixture can be diluted with an aqueous base to easily isolate the coordination complex as a soluble salt from any less-soluble byproducts that may form. Filtration, decantation, or a similar separation technique can be used to separate any insoluble material that may be present. In some instances, a mixture of aqueous bases can be used to form coordination complexes containing multiple counterions, such as a mixture of $Na^+$ and $K^+$ counterions. By forming coordination complexes having mixed counterions, the aqueous solubility of the coordination complexes can be further increased in some instances. In sum, the processes described herein can readily provide high-concentration aqueous solutions of coordination complexes having both unsubstituted catecholate ligands and monosulfonated catecholate ligands. Such coordination complexes and their aqueous solutions can be highly desirable for use in flow batteries and other types of electrochemical systems.

In addition to improved solubility, coordination complexes of the present disclosure can provide further advantages as well. In particular, the highly ionized sulfonic acid group can improve the ionic conductivity of electrolyte solutions in which such coordination complexes are present. By utilizing the coordination complexes of the present disclosure, particularly aqueous solutions of such coordination complexes, one can avoid adding an extraneous electrolyte to electrolyte solutions in which the coordination complexes are present, or the amount of extraneous electrolyte can be significantly decreased. Not only can omission or decrease in the amount of extraneous electrolyte reduce cost of goods, but it can also ultimately allow higher-concentration electrolyte solutions of the coordination complexes to be realized, such as through minimizing common-ion effects. Decreased crossover of the charged active material across the separator of a flow battery can also result.

In various embodiments, the present disclosure describes compositions containing a coordination complex including at least one unsubstituted catecholate ligand and at least one monosulfonated catecholate ligand or a salt thereof. Flow batteries and related electrochemical systems containing an aqueous solution of such coordination complexes as an electrolyte solution are also disclosed herein. Further disclosure regarding flow batteries containing such coordination complexes and their operating characteristics are also discussed in more detail below.

In some embodiments, coordination complexes of the present disclosure can include a metal center having at least one unsubstituted catecholate ligand and at least one monosulfonated catecholate ligand bound thereto. In some embodiments, the at least one monosulfonated catecholate ligand can be 3,4-dihydroxybenzenesulfonic acid. In more particular embodiments, compositions containing such coordination complexes can include an aqueous solution having an alkaline pH in which the coordination complex is dissolved. In such embodiments, the coordination complexes can bear an overall negative charge and have at least one positively charged monovalent counterion associated therewith that maintains charge balance.

In some embodiments, the coordination complexes disclosed herein can include a transition metal. Due to their variable oxidation states, transition metals can be highly desirable for use within the active material of a flow battery. Cycling between the accessible oxidation states can result in the conversion of chemical energy into electrical energy. Lanthanide metals can be used similarly in this regard in alternative embodiments. In general, any transition metal or lanthanide metal can be present as the metal center in the coordination complexes of the present disclosure. In more specific embodiments, the metal center can be a transition metal selected from among Al, Cr, Ti and Fe. For purposes of the present disclosure, Al is to be considered a transition metal. In more specific embodiments, the transition metal can be Ti. Other suitable transition and main group metals that can be present in the coordination complexes of the present disclosure include, for example, Ca, Ce, Co, Cu, Mg, Mn, Mo, Ni, Pd, Pt, Ru, Sr, Sn, V, Zn, Zr, and any combination thereof. In various embodiments, the coordination complexes can include a transition metal in a non-zero oxidation state when the transition metal is in both its oxidized and reduced forms. Cr, Fe, Mn, Ti and V can be particularly desirable in this regard.

In some embodiments, coordination complexes of the present disclosure can have a formula of

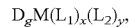

$$D_gM(L_1)_x(L_2)_y,$$

where M is a transition metal; D is a counterion selected from $H^+$, $NH_4^+$, tetraalkylammonium ($C_1$-$C_4$ alkyl), an alkali metal ion (e.g., $Li^+$, $Na^+$ or $K^+$), or any combination thereof, g ranges between 1 and 8; $L_1$ is an unsubstituted catecholate ligand; $L_2$ is a monosulfonated catecholate ligand or a salt thereof; and x and y are non-zero numbers such that x+y=3. The values of both x and y are not necessarily integers, although they can be in some embodiments.

In more specific embodiments of the present disclosure, the coordination complexes can contain titanium as a transition metal and have a formula of

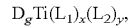

$$D_gTi(L_1)_x(L_2)_y,$$

where D is a counterion selected from $NH_4^+$, $Li^+$, $Na^+$, $K^+$, or any combination thereof; g ranges between 2 and 6; $L_1$ is the unsubstituted catecholate ligand; $L_2$ is the monosulfonated catecholate ligand or the salt thereof, and x and y are non-zero numbers such that x+y=3. The values of both x and y are not necessarily integers, although they can be in some embodiments. In some embodiments, D can be chosen from among $Li^+$, $Na^+$, $K^+$, or any combination thereof, and in some more specific embodiments, D can be chosen such that the coordination complex contains both $Na^+$ and $K^+$ counterions.

In some embodiments, g, x and y can have integer values. However, non-integer values of these variables are also possible. In one non-limiting example, x and y can have non-integer values when the compositions contain a multiple coordination complexes of the type described herein. For example, compositions of the present disclosure can include an overall complex stoichiometry of $D_gM(L_1)_x(L_2)_y$, with non-integer values of x and y if multiple coordination complexes are present in unequal amounts. Non-integer values of x and y can also occur if the sulfonation reaction leaves more than 2 equivalents of unsubstituted catechol compared to the amount of monosulfonated catechol that is produced.

In more particular embodiments of the present disclosure, the coordination complexes described herein can have integer values of x and y. Illustrative coordination complexes of this type can include $D_gM(L_1)_2(L_2)$ and $D_gM(L_1)(L_2)_2$, for example, such as those coordination complexes in which M is Ti or another transition metal. In some embodiments, the compositions can contain a single coordination complex of the foregoing type.

In still more specific embodiments, coordination complexes of the present disclosure with integer values of x and y can include those of the type $D_gTi(L_1)_2(L_2)$, where g=3 or 4, or $D_gTi(L_1)(L_2)_2$, where g=4 or 5. In more specific embodiments, D can include a mixture of $Na^+$ and $K^+$ so that the coordination complexes contain a mixture of these counterions.

More specifically, in some embodiments, coordination complexes of the present disclosure can have a formula of

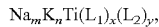

$Na_mK_nTi(L_1)_x(L_2)_y$, where 2≤m+n≤6, and $L_1$, $L_2$, x and y are defined as above. Both m and n are non-zero numbers, and they can be equal or non-equal to one another. In some embodiments, substantially equimolar amounts of $Na^+$ and $K^+$ counterions can be present, such that m and n are equal to one another. The values of both x and y are not necessarily integers, although they can be in some embodiments. In some embodiments, a ratio of m to n can range between about 1:10 to about 10:1, or between about 1:5 or about 5:1.

In some embodiments, other ligands can be present in the coordination complexes in combination with the unsubstituted catecholate ligands and the monosulfonated catecholate ligands. Other ligands that can be present in the coordination complexes include, for example, ascorbate, citrate, glycolate, a polyol, gluconate, hydroxyalkanoate, acetate, formate, benzoate, malate, maleate, phthalate, sarcosinate, salicylate, oxalate, urea, polyamine, aminophenolate, acetylacetonate, and lactate. Where chemically feasible, it is to be recognized that such ligands can be optionally substituted with at least one group selected from among $C_{1-6}$ alkoxy, $C_{1-6}$ alkyl, $C_{1-6}$ alkenyl, $C_{1-6}$ alkynyl, 5- or 6-membered aryl or heteroaryl groups, a boronic acid or a derivative thereof, a carboxylic acid or a derivative thereof, cyano, halide, hydroxyl, nitro, sulfonate, a sulfonic acid or a derivative thereof, a phosphonate, a phosphonic acid or a derivative thereof, or a glycol, such as polyethylene glycol. Alkanoate includes any of the alpha, beta, and gamma forms of these ligands. Polyamines include, but are not limited to, ethylenediamine, ethylenediamine tetraacetic acid (EDTA), and diethylenetriamine pentaacetic acid (DTPA).

Other examples of ligands that can be present in the coordination complexes in combination with the unsubstituted catecholate ligands and the monosulfonated catecholate ligands and/or any of the other aforementioned ligands can include monodentate, bidentate, and/or tridentate ligands. Examples of monodentate ligands that can be present in the coordination complexes of the present disclosure include, for example, carbonyl or carbon monoxide, nitride, oxo, hydroxo, water, sulfide, thiols, pyridine, pyrazine, and the like. Examples of bidentate ligands that can be present in the coordination complexes of the present disclosure include, for example, bipyridine, bipyrazine, ethylenediamine, diols (including ethylene glycol), and the like. Examples of tridentate ligands that can be present in the coordination complexes of the present disclosure include, for example, terpyridine, diethylenetriamine, triazacyclononane, tris(hydroxymethyl)aminomethane, and the like.

In some embodiments, compositions of the present disclosure can include an aqueous solution in which the coordination complex is dissolved. Such aqueous solutions can be employed as at least one of the electrolyte solutions in a flow battery or a related electrochemical system. Further disclosure regarding the aqueous solutions and their incorporation in flow batteries is provided hereinafter.

As used herein, the term "aqueous solution" will refer to a homogeneous liquid phase with water as a predominant solvent in which a coordination complex of the present disclosure is at least partially dissolved, ideally fully dissolved. This definition encompasses both solutions in water and solutions containing a water-miscible organic solvent as a minority component of an aqueous phase.

Illustrative water-miscible organic solvents that can be present in the aqueous solution include, for example, alcohols and glycols, optionally in the presence of one or more surfactants or other components discussed below. In more specific embodiments, the aqueous solution can contain at least about 98% water by weight. In other more specific embodiments, the aqueous solution can contain at least about 55% water by weight, or at least about 60% water by weight, or at least about 65% water by weight, or at least about 70% water by weight, or at least about 75% water by weight, or at least about 80% water by weight, or at least about 85% water by weight, or at least about 90% water by weight, or at least about 95% water by weight. In some embodiments, the aqueous solution can be free of water-miscible organic solvents and consist of water alone as a solvent.

In further embodiments, the aqueous solution can include a viscosity modifier, a wetting agent, or any combination thereof. Suitable viscosity modifiers can include, for example, corn starch, corn syrup, gelatin, glycerol, guar gum, pectin, and the like. Other suitable examples will be familiar to one having ordinary skill in the art. Suitable wetting agents can include, for example, various non-ionic surfactants and/or detergents. In some or other embodiments, the aqueous solution can further include a glycol or a polyol. Suitable glycols can include, for example, ethylene glycol, diethylene glycol, and polyethylene glycol. Suitable polyols can include, for example, glycerol, mannitol, sorbitol, pentaerythritol, and tris(hydroxymethyl)aminomethane. Inclusion of any of these components in the aqueous solution can help promote dissolution of the coordination complex and/or reduce viscosity of the aqueous solution for conveyance through a flow battery, for example.

In illustrative embodiments, the aqueous solution can have an alkaline pH. Alkaline pH values can be particularly desirable for promoting stability of coordination complexes containing catecholate ligands. In addition, alkaline pH values can maintain the sulfonic acid group of sulfonated catecholate ligands in a deprotonated state, thereby further enhancing solubility. As used herein, the term "alkaline pH" will refer to any pH value between about 7 and about 14. In some embodiments, one or more buffers can be present in the aqueous solution to help maintain the pH at an alkaline pH value. In more specific embodiments, the aqueous solution can be maintained at a pH of about 9 to about 12. A pH value residing within a range of about 9 to about 12 can be particularly desirable for maintaining the phenolic groups of catecholate ligands in a deprotonated state and complexed to the metal center of the coordination complex. Other illustrative alkaline pH ranges that can be maintained in the aqueous solutions include, for example, about 7 to about 7.5, or about 7.5 to about 8, or about 8 to about 8.5, or about 8.5 to about 9, or about 9.5 to about 10, or about 10 to about 10.5, or about 10.5 to about 11, or about 11 to about 11.5, or about 11.5 to about 12, or about 12 to about 12.5, or about 12.5 to about 13, or about 13 to about 13.5, or about 13.5 to about 14. Illustrative buffers that can be present include, but are not limited to, salts of phosphates, borates, carbonates, silicates, tris(hydroxymethyl)aminomethane (TRIS), 4-(2-hydroxyethyl)-1-piperazineethanesulfonic acid (HEPES), piperazine-N,N'-bis(ethanesulfonic acid) (PIPES), or any combination thereof.

In addition to a solvent and a coordination complex as an active material, the aqueous solutions can also include one or more mobile ions (i.e., an extraneous electrolyte) for use as an electrolyte solution in a flow battery or similar electrochemical system. In some embodiments, suitable mobile ions can include proton, hydronium, or hydroxide. In other various embodiments, mobile ions other than proton, hydronium, or hydroxide can be present, either alone or in combination with proton, hydronium or hydroxide. Such alternative mobile ions can include, for example, alkali metal or alkaline earth metal cations (e.g., $Li^+$, $Na^+$, $K^+$, $Mg^{2+}$, $Ca^{2+}$ and $Sr^{2+}$) and halides (e.g., $F^-$, $Cl^-$, or $Br^-$). Other suitable mobile ions can include, for example, ammonium and tetraalkylammonium ions, chalcogenides, phosphate, hydrogen phosphate, phosphonate, nitrate, sulfate, nitrite, sulfite, perchlorate, tetrafluoroborate, hexafluorophosphate, and any combination thereof. In some embodiments, less than about 50% of the mobile ions can constitute protons, hydronium, or hydroxide. In other various embodiments, less than about 40%, less than about 30%, less than about 20%, less than about 10%, less than about 5%, or less than about 2% of the mobile ions can constitute protons, hydronium, or hydroxide.

In other various embodiments, aqueous solutions containing coordination complexes of the present disclosure can lack an extraneous electrolyte altogether. As indicated above, the highly ionized sulfonic acid group of the monosulfonated catecholate ligand(s) within the coordination complex can provide sufficient ionic conductivity for use as an electrolyte solution in many instances. In some embodiments, the aqueous solutions of the present disclosure can have ionic conductivity values up to about 80 mS/cm at 45° C. The conductivity values can vary due to the concentration of the active material and/or due to the concentration of any extraneous electrolytes that are present.

In various embodiments, a concentration of the coordination complex in the aqueous solution can range between about 0.1 M and about 3 M. In an electrolyte solution, this concentration range represents the sum of the individual concentrations of the oxidized and reduced forms of the coordination complex. In more particular embodiments, the concentration of the coordination complex can range between about 0.5 M and about 3 M, or between 1 M and about 3 M, or between about 1.5 M and about 3 M, or between 1 M and about 2.5 M. Various solubility-promoting additives can lead to higher solubility values than are possible with the coordination complex alone.

As indicated above, aqueous solutions of the present disclosure can be incorporated in flow batteries and related electrochemical systems. Further disclosure on suitable flow batteries and their operating parameters follows hereinafter.

Accordingly, in various embodiments, flow batteries of the present disclosure can include a first half-cell having a first electrolyte solution therein, where the first electrolyte solution is an aqueous solution containing a coordination complex having at least one unsubstituted catecholate ligand and at least one monosulfonated catecholate ligand or a salt thereof that is bound to a metal center, as defined hereinabove. In some embodiments, the coordination complex can have a formula of

where M is a transition metal; D is a counterion selected from $H^+$, $NH_4^+$, tetraalkylammonium ($C_1$-$C_4$ alkyl), an alkali metal ion (e.g., $Li^+$, $Na^+$ or $K^+$), or any combination thereof; g ranges between 1 and 8; $L_1$ is the unsubstituted catecholate ligand; $L_2$ is the monosulfonated catecholate ligand; and x and y are non-zero numbers such that x+y=3. The values of both x and y are not necessarily integers, although they can be in some embodiments. In more specific embodiments, the coordination complex within the first electrolyte solution can be a titanium complex having a formula of

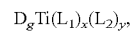

where D is a counterion selected from $NH_4^+$, $Li^+$, $Na^+$, $K^+$, or any combination thereof; g ranges between 2 and 6; $L_1$ is the unsubstituted catecholate ligand; $L_2$ is the monosulfonated catecholate ligand; and x and y are non-zero numbers such that x+y=3. The values of both x and y are not necessarily integers, although they can be in some embodiments. Additional disclosure regarding such coordination complexes is provided hereinabove.

In further embodiments, flow batteries of the present disclosure can also include a second half-cell having a second electrolyte solution therein, where the second electrolyte solution contains an active material differing from that in the first electrolyte solution. In more specific embodiments, the second electrolyte solution can be an aqueous solution containing an iron hexacyanide complex. Iron hexacyanide complexes can be particularly desirable active materials due to their facile electrode kinetics and substantially reversible electrochemical behavior within the working electrochemical window of aqueous solutions. Hence, these complexes can allow high open circuit potentials and cell efficiencies to be realized, particularly in combination with titanium catecholate complexes as the active material in the first electrolyte solution. In more specific embodiments, flow batteries of the present disclosure can include the first electrolyte solution in contact with a negative electrode of the flow battery and the second electrolyte solution in contact with the positive electrode of the flow battery.

Illustrative flow battery configurations that can incorporate the foregoing electrolyte solutions and coordination complexes will now be described in further detail. The flow batteries of the present disclosure are, in some embodiments, suited to sustained charge or discharge cycles of several hour durations. As such, they can be used to smooth energy supply/demand profiles and provide a mechanism for stabilizing intermittent power generation assets (e.g., from renewable energy sources such as solar and wind energy). It should be appreciated, then, that various embodiments of the present disclosure include energy storage applications where such long charge or discharge durations are desirable. For example, in non-limiting examples, the flow batteries of the present disclosure can be connected to an electrical grid to allow renewables integration, peak load shifting, grid firming, baseload power generation and consumption, energy arbitrage, transmission and distribution asset deferral, weak grid support, frequency regulation, or any combination thereof. When not connected to an electrical grid, the flow batteries of the present disclosure can be used as power sources for remote camps, forward operating bases, off-grid telecommunications, remote sensors, the like, and any combination thereof. Further, while the disclosure herein is generally directed to flow batteries, it is to be appreciated that other electrochemical energy storage media can incorporate the electrolyte solutions and coordination complexes described herein, specifically those utilizing stationary electrolyte solutions.

In some embodiments, flow batteries of the present disclosure can include: a first chamber containing a negative electrode contacting a first aqueous electrolyte solution; a second chamber containing a positive electrode contacting a second aqueous electrolyte solution, and a separator disposed between the first and second electrolyte solutions. The chambers provide separate reservoirs within the cell, through which the first and/or second electrolyte solutions circulate so as to contact the respective electrodes and the separator. Each chamber and its associated electrode and electrolyte solution define a corresponding half-cell. The separator provides several functions which include, for example, (1) serving as a barrier to mixing of the first and second electrolyte solutions, (2) electrically insulating to reduce or prevent short circuits between the positive and negative electrodes, and (3) to facilitate ion transport between the positive and negative electrolyte chambers, thereby balancing electron transport during charge and discharge cycles. The negative and positive electrodes provide a surface where electrochemical reactions can take place during charge and discharge cycles. During a charge or discharge cycle, electrolyte solutions can be transported from separate storage tanks through the corresponding chambers. In a charging cycle, electrical power can be applied to the cell such that the active material contained in the second electrolyte solution undergoes a one or more electron oxidation and the active material in the first electrolyte solution undergoes a one or more electron reduction. Similarly, in a discharge cycle the second active material is reduced and the first active material is oxidized to generate electrical power.

In more specific embodiments, illustrative flow batteries of the present disclosure can include: (a) a first aqueous electrolyte solution containing a first coordination complex; (b) a second aqueous electrolyte solution containing a second coordination complex; (c) a separator positioned between said first and second aqueous electrolyte solutions; and (d) an optional mobile ion in the first and second aqueous electrolyte solutions. As described in more detail below, the separator can be an ionomer membrane, and it can have a thickness of less than 100 microns and have an associated net charge that is the same sign as that of the first and second coordination complexes.

FIG. 1 depicts a schematic of an illustrative flow battery. Unlike typical battery technologies (e.g., Li-ion, Ni-metal hydride, lead-acid, and the like), where active materials and other components are housed in a single assembly, flow batteries transport (e.g., via pumping) redox active energy storage materials from storage tanks through an electrochemical stack. This design feature decouples the electrical energy storage system power from the energy storage capacity, thereby allowing for considerable design flexibility and cost optimization.

As shown in FIG. 1, flow battery system 1 includes an electrochemical cell that features separator 20 (e.g., a membrane) that separates the two electrodes 10 and 10' of the electrochemical cell. Electrodes 10 and 10' are formed from a suitably conductive material, such as a metal, carbon, graphite, and the like. Tank 50 contains first active material 30, which is capable of being cycled between an oxidized state and a reduced state.

Pump 60 affects transport of first active material 30 from tank 50 to the electrochemical cell. The flow battery also suitably includes second tank 50' that contains second active material 40. Second active material 40 can be the same material as active material 30, or it can be different. Second pump 60' can affect transport of second active material 40 to the electrochemical cell. Pumps can also be used to affect transport of the active materials from the electrochemical cell back to tanks 50 and 50' (not shown in FIG. 1). Other methods of affecting fluid transport, such as siphons, for example, can also suitably transport first and second active materials 30 and 40 into and out of the electrochemical cell. Also shown in FIG. 1 is power source or load 70, which completes the circuit of the electrochemical cell and allows a user to collect or store electricity during its operation.

It should be understood that FIG. 1 depicts a specific, non-limiting embodiment of a flow battery. Accordingly, flow batteries consistent with the spirit of the present disclosure can differ in various aspects relative to the configuration of FIG. 1. As one example, a flow battery system can include one or more active materials that are solids, gases, and/or gases dissolved in liquids. Active materials can be stored in a tank, in a vessel open to the atmosphere, or simply vented to the atmosphere.

As used herein, the terms "separator" and "membrane" refer to an ionically conductive and electrically insulating material disposed between the positive and negative electrodes of an electrochemical cell. The separator can be a porous membrane in some embodiments and/or an ionomer membrane in other various embodiments. In some embodiments, the separator can be formed from an ionically conductive polymer.

Polymer membranes can be anion- or cation-conducting electrolytes. Where described as an "ionomer," the term refers to polymer membrane containing both electrically neutral repeating units and ionized repeating units, where the ionized repeating units are pendant and covalently bonded to the polymer backbone. In general, the fraction of ionized units can range from about 1 mole percent to about 90 mole percent. For example, in some embodiments, the content of ionized units is less than about 15 mole percent; and in other embodiments, the ionic content is higher, such as greater than about 80 mole percent. In still other embodiments, the ionic content is defined by an intermediate range, for example, in a range of about 15 to about 80 mole percent. Ionized repeating units in an ionomer can include anionic functional groups such as sulfonate, carboxylate, and the like. These functional groups can be charge balanced by, mono-, di-, or higher-valent cations, such as alkali or alkaline earth metals. Ionomers can also include polymer compositions containing attached or embedded quaternary ammonium, sulfonium, phosphazenium, and guanidinium residues or salts. Suitable examples will be familiar to one having ordinary skill in the art.

In some embodiments, polymers useful as a separator can include highly fluorinated or perfluorinated polymer backbones. Certain polymers useful in the present disclosure can include copolymers of tetrafluoroethylene and one or more fluorinated, acid-functional co-monomers, which are commercially available as NAFION™ perfluorinated polymer electrolytes from DuPont. Other useful perfluorinated polymers can include copolymers of tetrafluoroethylene and $FSO_2$—$CF_2CF_2CF_2CF_2$—O—$CF$=$CF_2$, FLEMION™ and SELEMION™.

Additionally, substantially non-fluorinated membranes that are modified with sulfonic acid groups (or cation exchanged sulfonate groups) can also be used. Such membranes can include those with substantially aromatic backbones such as, for example, polystyrene, polyphenylene, biphenyl sulfone (BPSH), or thermoplastics such as polyetherketones and polyethersulfones.

Battery-separator style porous membranes, can also be used as the separator. Because they contain no inherent ionic conduction capabilities, such membranes are typically impregnated with additives in order to function. These membranes typically contain a mixture of a polymer and inorganic filler, and open porosity. Suitable polymers can include, for example, high density polyethylene, polypropylene, polyvinylidene difluoride (PVDF), or polytetrafluoroethylene (PTFE). Suitable inorganic fillers can include silicon carbide matrix material, titanium dioxide, silicon dioxide, zinc phosphide, and ceria.

Separators can also be formed from polyesters, polyetherketones, poly(vinyl chloride), vinyl polymers, and substituted vinyl polymers. These can be used alone or in combination with any previously described polymer.

Porous separators are non-conductive membranes which allow charge transfer between two electrodes via open channels filled with electrolyte. The permeability increases the probability of chemicals (e.g., active materials) passing through the separator from one electrode to another and causing cross-contamination and/or reduction in cell energy efficiency. The degree of this cross-contamination can depend on, among other features, the size (the effective diameter and channel length), and character (hydrophobicity/hydrophilicity) of the pores, the nature of the electrolyte, and the degree of wetting between the pores and the electrolyte.

The pore size distribution of a porous separator is generally sufficient to substantially prevent the crossover of active materials between the two electrolyte solutions. Suitable porous membranes can have an average pore size distribution of between about 0.001 nm and 20 micrometers, more typically between about 0.001 nm and 100 nm. The size distribution of the pores in the porous membrane can be substantial. In other words, a porous membrane can contain a first plurality of pores with a very small diameter (approximately less than 1 nm) and a second plurality of pores with a very large diameter (approximately greater than 10 micrometers). The larger pore sizes can lead to a higher amount of active material crossover. The ability for a porous membrane to substantially prevent the crossover of active materials can depend on the relative difference in size between the average pore size and the active material. For example, when the active material is a metal center in a coordination complex, the average diameter of the coordination complex can be about 50% greater than the average pore size of the porous membrane. On the other hand, if a porous membrane has substantially uniform pore sizes, the average diameter of the coordination complex can be about 20% larger than the average pore size of the porous membrane. Likewise, the average diameter of a coordination complex is increased when it is further coordinated with at least one water molecule. The diameter of a coordination complex of at least one water molecule is generally considered to be the hydrodynamic diameter. In such embodiments, the hydrodynamic diameter is generally at least about 35% greater than the average pore size. When the average pore size is substantially uniform, the hydrodynamic radius can be about 10% greater than the average pore size.

In some embodiments, the separator can also include reinforcement materials for greater stability. Suitable reinforcement materials can include nylon, cotton, polyesters, crystalline silica, crystalline titania, amorphous silica, amorphous titania, rubber, asbestos, wood or any combination thereof.

Separators within the flow batteries of the present disclosure can have a membrane thickness of less than about 500 micrometers, or less than about 300 micrometers, or less than about 250 micrometers, or less than about 200 micrometers, or less than about 100 micrometers, or less than about 75 micrometers, or less than about 50 micrometers, or less than about 30 micrometers, or less than about 25 micrometers, or less than about 20 micrometers, or less than about 15 micrometers, or less than about 10 micrometers. Suitable separators can include those in which the flow battery is capable of operating with a current efficiency of greater than about 85% with a current density of 100 mA/cm$^2$ when the separator has a thickness of 100 micrometers. In further embodiments, the flow battery is capable of operating at a current efficiency of greater than 99.5% when the separator has a thickness of less than about 50 micrometers, a current efficiency of greater than 99% when the separator has a thickness of less than about 25 micrometers, and a current efficiency of greater than 98% when the separator has a thickness of less than about 10 micrometers. Accordingly, suitable separators include those in which the flow battery is capable of operating at a voltage efficiency of greater than 60% with a current density of 100 mA/cm$^2$. In further embodiments, suitable separators can include those in which the flow battery is capable of operating at a voltage efficiency of greater than 70%, greater than 80% or even greater than 90%.

The diffusion rate of the first and second active materials through the separator can be less than about $1\times10^{-5}$ mol cm$^{-2}$ day$^{-1}$, or less than about $1\times10^{-6}$ mol cm$^2$ day$^{-1}$, or less than about $1\times10^{-7}$ mol cm$^{-2}$ day$^{-1}$, or less than about $1\times10^{-9}$ mol cm$^{-2}$ day$^{-1}$, or less than about $1\times10^{-11}$ mol cm$^{-2}$ day$^{-1}$, or less than about $1\times10^{-13}$ mol cm$^{-2}$ day$^{-1}$, or less than about $1\times10^{-15}$ mol cm$^{-2}$ day$^{-1}$.

The flow batteries can also include an external electrical circuit in electrical communication with the first and second electrodes. The circuit can charge and discharge the flow battery during operation. Reference to the sign of the net ionic charge of the first, second, or both active materials relates to the sign of the net ionic charge in both oxidized and reduced forms of the redox active materials under the conditions of the operating flow battery. The net ionic charge of the coordination complexes disclosed herein can vary based upon the number of deprotonated sulfonic acid groups that are present. Further exemplary embodiments of a flow battery provide that (a) the first active material has an associated net positive or negative charge and is capable of providing an oxidized or reduced form over an electric potential in a range of the negative operating potential of the system, such that the resulting oxidized or reduced form of the first active material has the same charge sign (positive or negative) as the first active material and the ionomer membrane also has a net ionic charge of the same sign; and (b) the second active material has an associated net positive or negative charge and is capable of providing an oxidized or reduced form over an electric potential in a range of the positive operating potential of the system, such that the resulting oxidized or reduced form of the second active material has the same charge sign (positive or negative sign) as the second active material and the ionomer membrane also has a net ionic charge of the same sign; or both (a) and (b). In the case of the first active material being a coordination complex bearing one or more sulfonated catecholate ligands, the net ionic charge in both the oxidized and reduced forms can be negative. The matching charges of the first and/or second active materials and the ionomer membrane can provide a high selectivity. More specifically, charge matching can provide less than about 3%, less than about 2%, less than about 1%, less than about 0.5%, less than about 0.2%, or less than about 0.1% of the molar flux of ions passing through the ionomer membrane as being attributable to the first or second active material. The term "molar flux of ions" will refer to the amount of ions passing through the ionomer membrane, balancing the charge associated with the flow of external electricity/electrons. That is, the flow battery is capable of operating or operates with the substantial exclusion of the active materials by the ionomer membrane, and such exclusion can be promoted through charge matching.

Flow batteries incorporating the electrolyte solutions of the present disclosure can have one or more of the following operating characteristics: (a) where, during the operation of the flow battery, the first or second active materials comprise less than about 3% of the molar flux of ions passing through the ionomer membrane; (b) where the round trip current efficiency is greater than about 70%, greater than about 80%, or greater than about 90%; (c) where the round trip current efficiency is greater than about 90%; (d) where the sign of the net ionic charge of the first, second, or both active materials is the same in both oxidized and reduced forms of the active materials and matches that of the ionomer membrane; (e) where the ionomer membrane has a thickness of less than about 100 µm, less than about 75 µm, less than about 50 µm, or less than about 250 µm; (f) where the flow battery is capable of operating at a current density of greater than about 100 mA/cm$^2$ with a round trip voltage efficiency of greater than about 60%; and (g) where the energy density of the electrolyte solutions is greater than about 10 Wh/L, greater than about 20 Wh/L, or greater than about 30 Wh/L.

In some cases, a user may desire to provide higher charge or discharge voltages than available from a single battery cell. In such cases, several battery cells can be connected in series such that the voltage of each cell is additive. This forms a bipolar stack. An electrically conductive, but non-porous material (e.g., a bipolar plate) can be employed to connect adjacent battery cells in a bipolar stack, which allows for electron transport but prevents fluid or gas transport between adjacent cells. The positive electrode compartments and negative electrode compartments of individual cells can be fluidically connected via common positive and negative fluid manifolds in the stack. In this way, individual cells can be stacked in series to yield a voltage appropriate for DC applications or conversion to AC applications.

In additional embodiments, the cells, cell stacks, or batteries can be incorporated into larger energy storage systems, suitably including piping and controls useful for operation of these large units. Piping, control, and other equipment suitable for such systems are known in the art, and can include, for example, piping and pumps in fluid communication with the respective chambers for moving electrolyte solutions into and out of the respective chambers and storage tanks for holding charged and discharged electrolytes. The cells, cell stacks, and batteries of this disclosure can also include an operation management system. The operation management system can be any suitable controller device, such as a computer or microprocessor, and can contain logic circuitry that sets operation of any of the various valves, pumps, circulation loops, and the like.

In more specific embodiments, a flow battery system can include a flow battery (including a cell or cell stack); storage tanks and piping for containing and transporting the electrolyte solutions; control hardware and software (which may include safety systems); and a power conditioning unit. The flow battery cell stack accomplishes the conversion of charging and discharging cycles and determines the peak power. The storage tanks contain the positive and negative active materials, such as the coordination complexes disclosed herein, and the tank volume determines the quantity of energy stored in the system. The control software, hardware, and optional safety systems suitably include sensors, mitigation equipment and other electronic/hardware controls and safeguards to ensure safe, autonomous, and efficient operation of the flow battery system. A power conditioning unit can be used at the front end of the energy storage system to convert incoming and outgoing power to a voltage and current that is optimal for the energy storage system or the application. For the example of an energy storage system connected to an electrical grid, in a charging cycle the power conditioning unit can convert incoming AC electricity into DC electricity at an appropriate voltage and current for the cell stack. In a discharging cycle, the stack produces DC electrical power and the power conditioning unit converts it to AC electrical power at the appropriate voltage and frequency for grid applications.

Where not otherwise defined hereinabove or understood by one having ordinary skill in the art, the definitions in the following paragraphs will be applicable to the present disclosure.

As used herein, the term "energy density" will refer to the amount of energy that can be stored, per unit volume, in the active materials. Energy density refers to the theoretical energy density of energy storage and can be calculated by Equation 1:

$$\text{Energy density} = (26.8 \text{ A-h/mol}) \times OCV \times [e^-] \tag{1}$$

where OCV is the open circuit potential at 50% state of charge, (26.8 A-h/mol) is Faraday's constant, and [e$^-$] is the concentration of electrons stored in the active material at 99% state of charge. In the case that the active materials largely are an atomic or molecular species for both the positive and negative electrolyte, [e$^-$] can be calculated by Equation 2 as:

$$[e^-] = [\text{active materials}] \times N/2 \tag{2}$$

where [active materials] is the molar concentration of the active material in either the negative or positive electrolyte, whichever is lower, and N is the number of electrons transferred per molecule of active material. The related term "charge density" will refer to the total amount of charge that each electrolyte contains. For a given electrolyte, the charge density can be calculated by Equation 3

$$\text{Charge density} = (26.8 \text{ A-h/mol}) \times [\text{active material}] \times N \tag{3}$$

where [active material] and N are as defined above.

As used herein, the term "current density" will refer to the total current passed in an electrochemical cell divided by the geometric area of the electrodes of the cell and is commonly reported in units of mA/cm$^2$.

As used herein, the term "current efficiency" ($I_{eff}$) can be described as the ratio of the total charge produced upon discharge of a cell to the total charge passed during charging. The current efficiency can be a function of the state of charge of the flow battery. In some non-limiting embodiments, the current efficiency can be evaluated over a state of charge range of about 35% to about 60%.

As used herein, the term "voltage efficiency" can be described as the ratio of the observed electrode potential, at a given current density, to the half-cell potential for that electrode (×100%). Voltage efficiencies can be described for a battery charging step, a discharging step, or a "round trip voltage efficiency." The round trip voltage efficiency ($V_{eff,rt}$) at a given current density can be calculated from the cell voltage at discharge ($V_{discharge}$) and the voltage at charge ($V_{charge}$) using equation 4:

$$V_{eff,RT} = V_{discharge}/V_{charge} \times 100\% \quad (4)$$

As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to a reversible hydrogen electrode. The negative electrode is associated with a first electrolyte solution and the positive electrode is associated with a second electrolyte solution, as described herein. The electrolyte solutions associated with the negative and positive electrodes may be described as negolytes and posolytes, respectively.

As indicated above, the present disclosure also provides methods for synthesizing monosulfonated catechols and coordination complexes containing such monosulfonated catechols as ligands. More particularly, the present disclosure further provides methods for synthesizing reaction mixtures containing a mixture of catechol and a monosulfonated catechol or a salt thereof, and then forming a coordination complex from the reaction product without separating the catechol and the monosulfonated catechol or the salt thereof from one another. Advantageously, such syntheses can include forming the reaction product and the coordination complexes consecutively in a single reaction vessel in some embodiments. That is, the synthetic methods of the present disclosure can include "one-pot" processes in which the reaction product is not transferred and/or purified before being utilized for complexation of a transition metal. In alternative embodiments, however, transfer of the reaction product to a secondary vessel and/or some extent of purification of the reaction product can take place while still being consistent with the scope of the present disclosure.

Accordingly, in various embodiments, methods for synthesizing a reaction product containing a monosulfonated catechol and then forming a coordination complex therefrom can include: providing a neat mixture of catechol and a sub-stoichiometric amount of sulfuric acid relative to the catechol; heating the neat mixture to form a reaction product containing a mixture of catechol and a monosulfonated catechol or a salt thereof; and without separating the catechol and the monosulfonated catechol or the salt thereof from one another, forming a coordination complex from the reaction product having a metal center with at least one unsubstituted catecholate ligand and at least one monosulfonated catecholate ligand bound thereto.

In some embodiments, the monosulfonated catechol can be a mixture of 2,3-dihydroxybenzenesulfonic acid and 3,4-dihydroxybenzenesulfonic acid or a salt thereof. Such mixtures can be formed at lower reaction temperatures, such as near room temperature.

In other embodiments, the monosulfonated catechol can be substantially 3,4-dihydroxybenzenesulfonic acid. This compound can be produced by conducting the sulfonation reaction under higher temperature conditions. Suitable temperature conditions for synthesizing 3,4-dihydroxybenzenesulfonic acid as the primary sulfonation product are discussed in greater detail hereinafter. Synthesizing the monosulfonated catechol as substantially a single isomer can provide coordination complexes having more consistent electrochemical performance than if mixture-isomer ligands are present. Moreover, by utilizing a stoichiometric deficit of sulfuric acid relative to catechol, the formation of disulfonated catechol can be significantly minimized or eliminated in the reaction product. Elimination of disulfonated catecholate ligands from the coordination complexes of the present disclosure can be desirable to avoid the difficulties associated with such complexes when they are utilized within electrolyte solutions, as discussed above.

In some embodiments, the neat mixture of catechol and sulfuric acid can be heated at a temperature of about 80° C. or above. Above about 80° C., formation of the 2,3-dihydroxybenzenesulfonic acid side product is not significant and the conversion of catechol to 3,4-dihydroxybenzenesulfonic acid can occur at a convenient rate, even in the presence of a sub-stoichiometric amount of sulfuric acid. If the reaction temperature is too high, some catechol can sublime from the neat mixture and increase the stoichiometric ratio of sulfuric acid to catechol accordingly, thereby increasing the tendency of the reaction to form a disulfonated catechol (e.g., 4,5-dihydroxy-1,3-benzenedisulfonic acid). Accordingly, in some embodiments, the neat mixture of catechol and sulfuric acid can be heated to a maximum temperature of about 130° C. In more specific embodiments, the neat mixture can be heated at a temperature ranging between about 80° C. and about 130° C. In more particular embodiments, the neat mixture can be heated at a temperature ranging between about 80° C. and about 110° C., or at a temperature ranging between about 80° C. and about 100° C. Closed reaction vessels, such as sealed tubes and pressure bombs, can allow even higher temperatures to be utilized.

As used herein, the term "sub-stoichiometric" will refer to the condition of a reactant being present at a stoichiometric deficit, such that the reactant is a limiting reactant. Hence, any reaction conditions in which sulfuric acid is used at a stoichiometric deficit relative to catechol fall within the scope of the present disclosure. In more specific embodiments of the present disclosure, the neat mixture can contain up to about 0.7 stoichiometric equivalents of sulfuric acid relative to catechol. As little as 0.1 stoichiometric equivalents of sulfuric acid can be used in some embodiments of the present disclosure. In more specific embodiments, the neat mixture can contain between about 0.1 stoichiometric equivalents and about 0.7 stoichiometric equivalents of sulfuric acid relative to catechol, or between about 0.2 stoichiometric equivalents and about 0.7 stoichiometric equivalents or sulfuric acid relative to catechol, or between about 0.1 stoichiometric equivalents and about 0.4 stoichiometric equivalents of sulfuric acid relative to catechol, or between about 0.3 stoichiometric equivalents and about 0.5 stoichiometric equivalents of sulfuric acid relative to catechol, or between about 0.5 stoichiometric equivalents and about 0.7 stoichiometric equivalents of sulfuric acid relative to catechol. Stoichiometric ratios differing from a 1:2 or 2:1 ratio of sulfuric acid to catechol can produce coordination complexes having non-integer proportions of catecholate and sulfonated catecholate ligands (e.g., both x and y are non-integer values in the formulas discussed above).

The chosen sub-stoichiometric amount of sulfuric acid relative to catechol can dictate the ratio of unsubstituted catecholate ligands to monosulfonated catecholate ligands that are present in the coordination complex following complexation. Even coordination complexes having less than a full stoichiometric equivalent of sulfonate catecholate ligand can be useful in some embodiments of the present disclosure. In the event that the reaction mixture itself does not contain a desired ratio of catechol to the monosulfonated catechol, additional catechol and/or monosulfonated catechol from an extraneous source can be added to the reaction product before forming the coordination complex. More desirably, however, the reaction product is used directly without further adjusting the amounts of catechol or sulfonated catechol that are present.

In more particular embodiments, the coordination complex can be a titanium coordination complex. When 3 or more equivalents of unreacted catechol and monosulfonated catechol are present relative to the titanium compound with which the reaction product is reacted, titanium coordination complexes bearing substantially only catecholate and sulfonated catecholate ligands can be formed. Accordingly, in more specific embodiments, methods of the present disclosure can provide coordination complexes having a formula of

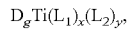

$D_g Ti(L_1)_x(L_2)_y$, where D is a counterion selected from $H^+$, $NH_4^+$, $Li^+$, $Na^+$, $K^+$, or any combination thereof; g ranges between 2 and 6; $L_1$ is the unsubstituted catecholate ligand; $L_2$ is the monosulfonated catecholate ligand or the salt thereof; and x and y are non-zero numbers such that x+y=3. The values of both x and y are not necessarily integers, although they can be in some embodiments. More particularly, immediately after forming the coordination complex from the reaction product, the counterion form of the titanium coordination complex can be in a protonated form, such that D is H. As discussed hereinafter, other counterion forms can also be formed following neutralization of the initially formed coordination complex.

In the case of titanium complexes, various titanium compounds, particularly Ti(IV) compounds, can be suitable for forming the coordination complex. In some embodiments, suitable titanium compounds can include titanium tetrachloride or titanium tetrakis(isopropoxide), for example, which can be reacted under non-aqueous reaction conditions to form the titanium complex. In other embodiments, an acidic aqueous solution of titanium oxychloride can be reacted with the 3,4-dihydrobenzenesulfonic acid to form the titanium coordination complex. The titanium oxychloride can be obtained commercially or can be generated in situ by slowly adding titanium tetrachloride to water under cooling conditions (<0° C.) that do not result in substantial formation of titanium dioxide, the typical reaction product formed upon interacting titanium tetrachloride with water. In still other embodiments, titanium nanoparticles can be reacted with a mixture of unsubstituted catechol and a monosulfonate catechol to form a coordination complex.

In further embodiments, methods of the present disclosure can include combining an organic solvent with the reaction product before forming the coordination complex. Introduction of an organic solvent to the reaction product can at least partially dissolve the reaction product and provide a more suitable medium for contacting the reaction product with a transition metal compound, for example. Choice of a suitable organic solvent can be dictated by the nature of the transition metal compound used to affect formation of the coordination complex. For example, in some instances, protic organic solvents such as methanol or other alcohols can be used. In other instances, the transition metal compound can be reactive with protic solvents, and aprotic solvents such as acetone, dimethylsulfoxide, N,N-dimethylformamide and like solvents can be used instead. In still other instances, non-polar organic solvents such as toluene or similar hydrocarbon solvents can be used suitably.

In some embodiments, methods of the present disclosure can further include combining at least one aqueous base with the coordination complex, and obtaining an aqueous solution of the coordination complex. In more specific embodiments, a sufficient amount of aqueous base can be added to the coordination complex to convert the initially produced protonated counterion form into another suitable counterion form, such as an alkali metal counterion form, for example. An aqueous alkaline solution of the coordination complex can be produced in this manner. Particular aqueous bases that can be suitable for use in the embodiments of the present disclosure include, for example, alkali metal hydroxides, alkali metal carbonates, alkali metal bicarbonates, ammonium hydroxide, ammonium carbonate, and ammonium bicarbonate. In more particular embodiments, the aqueous base can be ammonium hydroxide, lithium hydroxide, sodium hydroxide, potassium hydroxide, or any mixture thereof. In still more particular embodiments, a mixture of sodium hydroxide and potassium hydroxide can be combined with the initially formed coordination complex, thereby forming a coordination complex having both $Na^+$ and $K^+$ counterions.

Accordingly, in more specific embodiments of the present disclosure, methods for forming coordination complexes can include: providing a neat mixture of catechol and up to about 0.7 stoichiometric equivalents of sulfuric acid relative to the catechol; heating the neat mixture at a temperature of about 80° C. or above to form a reaction product containing a mixture of catechol and a monosulfonated catechol or a salt thereof, the monosulfonated catechol being 3,4-dihydroxybenzenesulfonic acid; without separating the catechol and the monosulfonated catechol or the salt thereof from one another, forming a coordination complex from the reaction product having a metal center with at least one unsubstituted catecholate ligand and at least one monosulfonated catecholate ligand bound thereto; combining an aqueous base with the coordination complex; and obtaining an aqueous solution of the coordination complex.

EXAMPLES

Example 1: Production of Monosulfonated Catechol

Neat mixtures containing various stoichiometric ratios of catechol and sulfuric acid were prepared and reacted at various temperatures and for various lengths of time. Particular reaction conditions are summarized in Table 1 below.

TABLE 1

| Entry | Equiv. $H_2SO_4$ | Temperature (°C.) | Reaction Time (hr) | Other Conditions | $^1$H NMR Ratio of Monosulfonated Catechol[1] to Unreacted Catechol | Amount of Disulfonated Catechol (Estimated from $^1$H NMR) |
|---|---|---|---|---|---|---|
| 1 | 0.9 | 100 | 4 | — | 78:22 | trace |
| 2 | 1.05 | 100 | 17 | — | 91:8 | 7 |
| 3 | 1.05 | 85 | 17 | — | 76:24 | trace |
| 4 | 0.9 | 100 | 17 | 3 Å molecular sieves | 74:26 | trace |
| 5 | 0.9 | 100 | 5 | 4 Å molecular sieves | 61:38 | trace |
| 6 | 1.05 | 100 | 4 | — | 93:7 | 4 |
| 7 | 1.05 | 100 | 2 | — | 92:8 | 3 |
| 8 | 1.2 | 100 | 4 | — | 97:3 | 6 |
| 9 | 1.05 | 100 | 3 | flowing $N_2$ | 59:41 | 4 |
| 10 | 1.05 | 100 | 3 | — | 92:8 | 3 |
| 11 | 1.05 | 100 | 0.5 | — | 84:16 | 6 |
| 12 | 0.33 | 85 | 3 | — | 32:68 | trace to none |
| 13 | 0.33 | 95 | 1 | — | 30:70 | trace to none |
| 14 | 0.33 | 115 | 2 | — | 32:68 | trace to none |
| 15 | 0.33 | 125 | 2 | — | 33:67 | trace to none |

Figure 2:
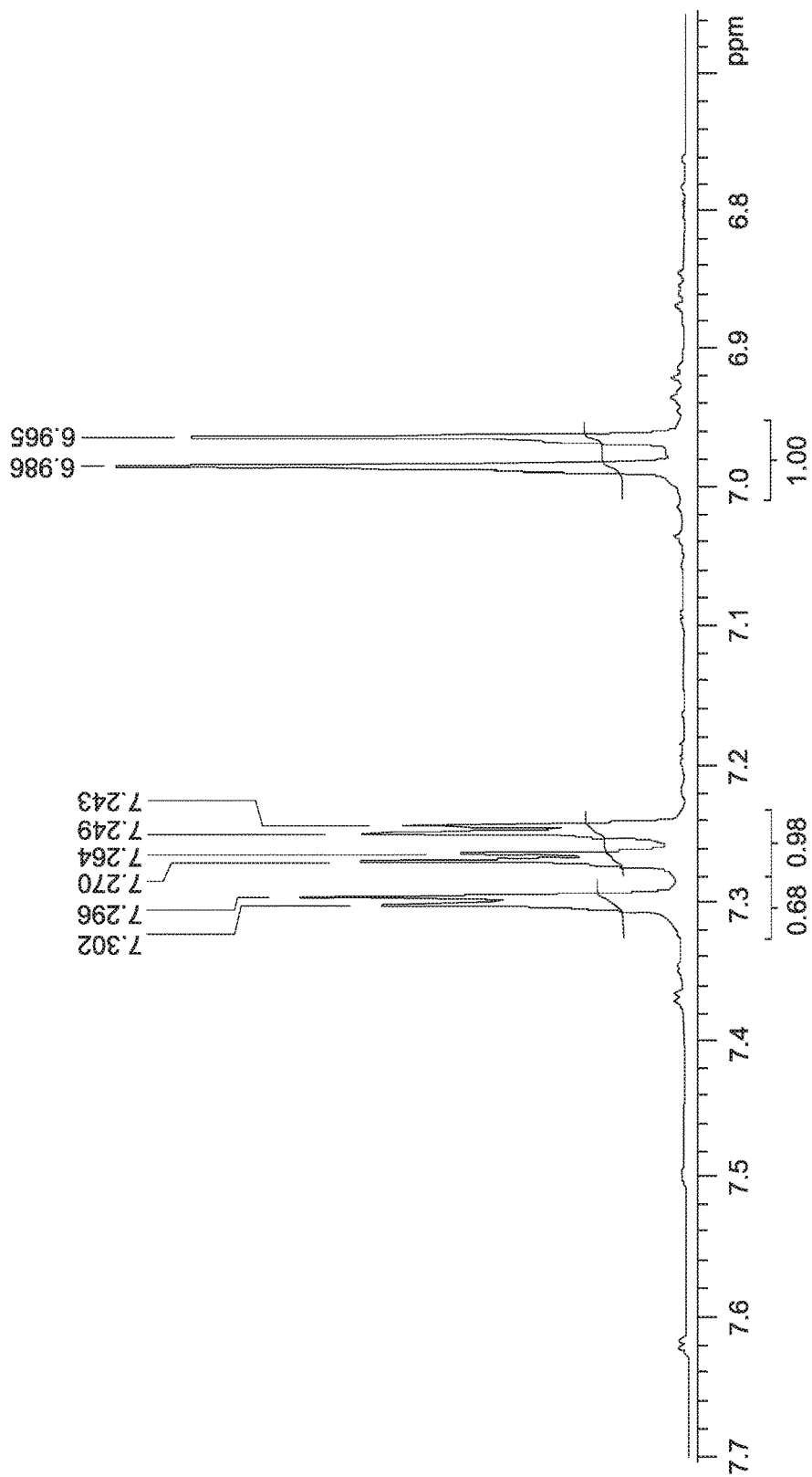
FIG. 2 shows an illustrative $^1$H NMR spectrum in $D_2O$ of the aromatic region of 3,4-dihydroxybenzenesulfonic acid following purification.

[1] 3,4-dihydrobenzenesulfonic acid
[2] <5% 2,3-dihydroxybenzenesulfonic acid was detected by $^1$H NMR Upon discontinuing heating, the reaction mixture was added to an ice/water mixture and was extracted 3 times with toluene. The aqueous phase was then evaporated to dryness, and 50% aqueous NaOH was then added to the resulting solid. The basic solution was then evaporated to dryness a second time. The solid was triturated successively with hot toluene and with methanol, each of which was then removed by decantation. The solids were filtered, washed with methanol and dried. In some instances, a second crop of product was recovered from the filtrate. In still further instances, the product was recrystallized from ethanol. FIG. 2 shows an illustrative $^1$H NMR spectrum in $D_2O$ of the aromatic region of 3,4-dihydroxybenzenesulfonic acid following purification.

As shown in Table 1, high ratios of the monosulfonated catechol relative to unreacted catechol resulted when a slight deficit to a slight stoichiometric excess of sulfuric acid was reacted with catechol. In contrast, when catechol was significantly present in excess (Entries 12-15), near-complete stoichiometric conversion of the sulfuric acid to monosulfonated catechol occurred along with a corresponding amount of unreacted catechol.

Figure 3:
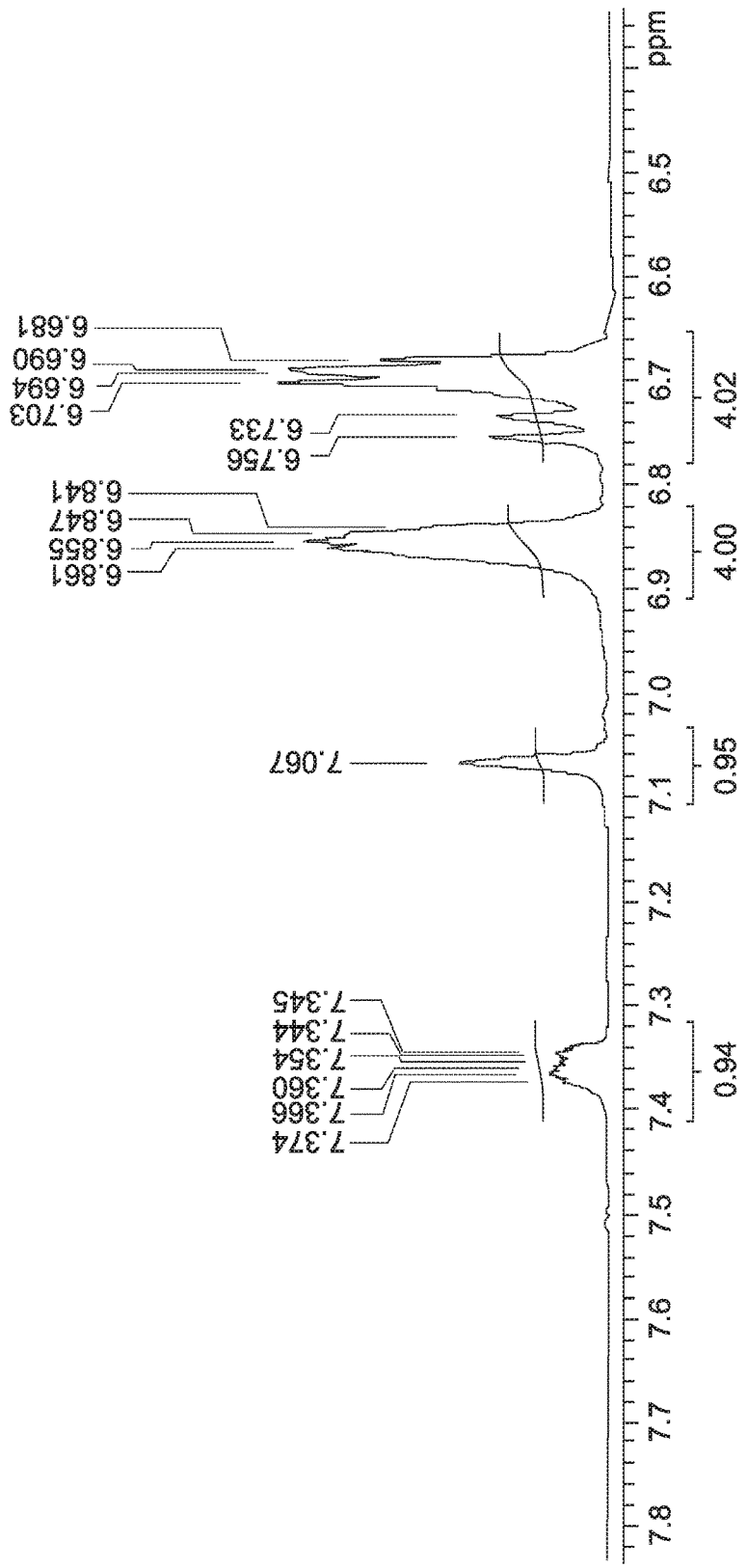
FIG. 3 shows an illustrative $^1$H NMR spectrum in $D_2O$ of the aromatic region of the titanium coordination complex formed from 2 equivalents of catechol and 1 equivalent of 3,4-dihydroxybenzenesulfonic acid.

Example 2: Formation of a Sulfonated Catecholate Coordination Complex Using Previously Isolated Monosulfonated Catechol A mixture containing 2 equivalents of catechol and 1 equivalent of 3,4-dihydroxybenzenesulfonic acid was mixed with methanol, and titanium tetrakis(isopropoxide) was added slowly over a period of time. The 3,4-dihydroxybenzenesulfonic acid was previously isolated from unreacted catechol and other side reaction products as described above. Distillation was conducted upon completion of the addition, and aqueous base was added to form a corresponding salt of the sulfonated catecholate complex in an aqueous solution. For example, addition of an equimolar mixture of aqueous sodium hydroxide and potassium hydroxide produced a mixed sodium/potassium salt of the sulfonated catecholate complex. FIG. 3 shows an illustrative $^1$H NMR spectrum in $D_2O$ of the aromatic region of the titanium complex formed from 2 equivalents of catechol and 1 equivalent of 3,4-dihydroxybenzenesulfonic acid.

Figure 4:
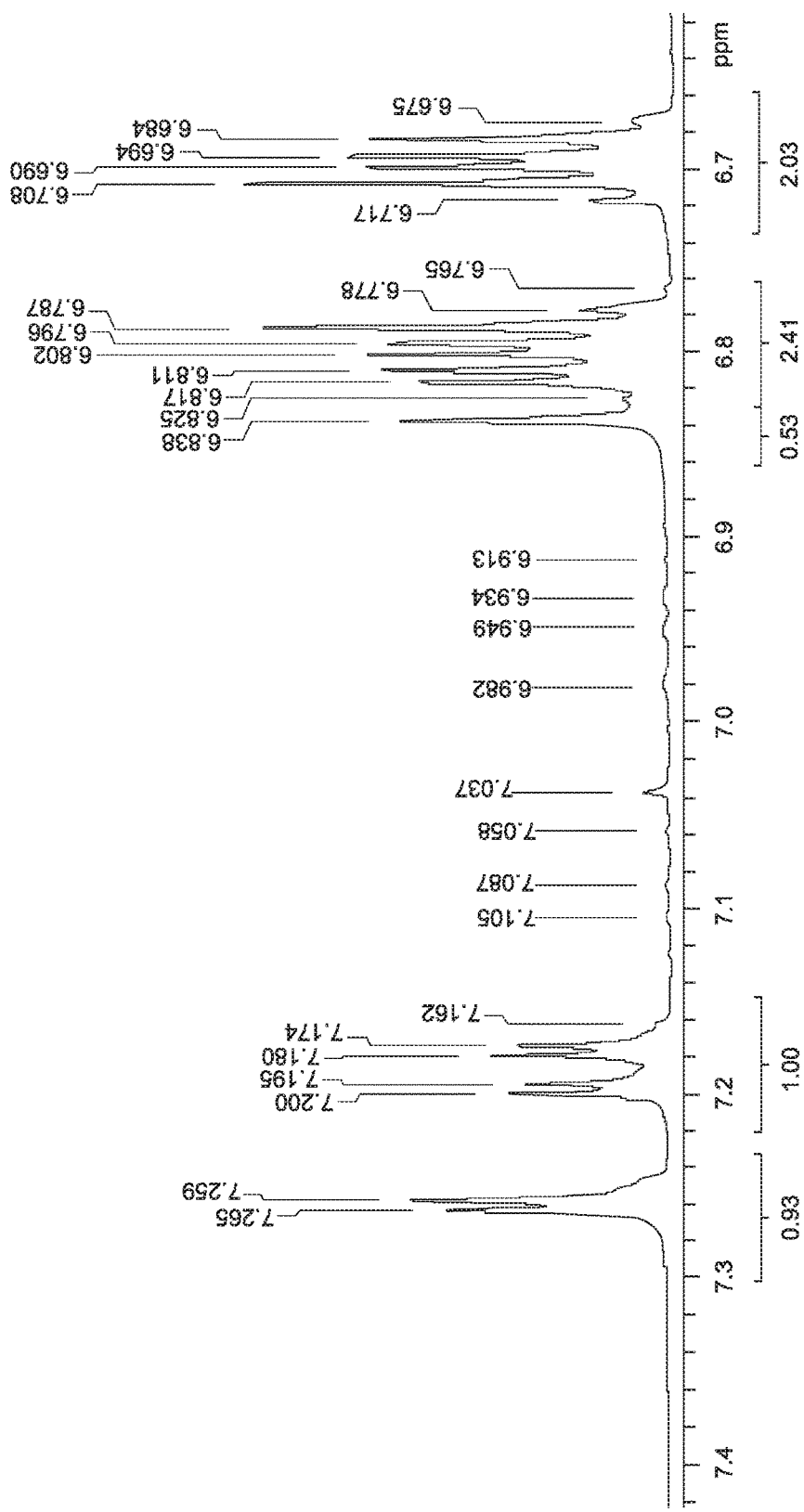
FIG. 4 shows an illustrative $^1$H NMR spectrum in $CD_3OD$ of the aromatic region of the titanium complex formed from 2 equivalents of catechol and 1 equivalent of 3,4-dihydroxybenzenesulfonic acid before addition of base.
Figure 5:
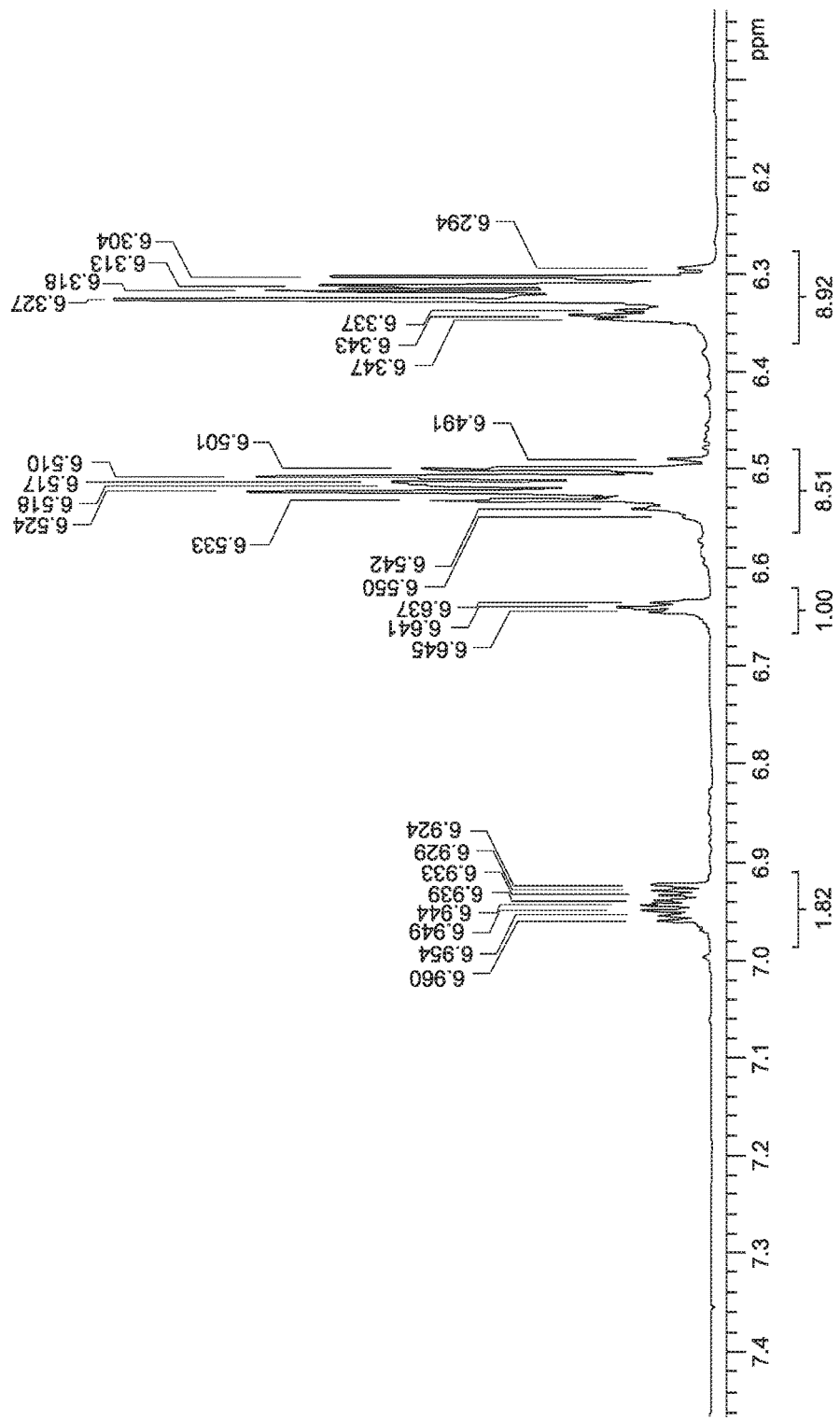
FIG. 5 shows an illustrative $^1$H NMR spectrum in $D_2O$ of the aromatic region of the titanium complex formed from 2 equivalents of catechol and 1 equivalent of 3,4-dihydroxybenzenesulfonic acid after addition of base.

Example 3: Formation of a Sulfonated Catecholate Coordination Complex Using an As-Produced Mixture of Catechol and Monosulfonated Catechol A neat mixture containing catechol (49.58 g, 3 stoichiometric equivalents) and sulfuric acid (8.0 mL, 1 stoichiometric equivalent) was heated at 115° C. for 2 hours. Xylenes was added to the hot purple reaction mixture, and the combined mixture was then cooled to room temperature. Titanium tetrachloride (16.5 mL, 1 stoichiometric equivalent) was then added to the combined mixture over 15 minutes, and the reaction mixture was then heated to 115° C. for 3 hours. HCl gas formation was visibly evident during the initial heating period. The reaction mixture was the left to cool at room temperature overnight, and a 6 M NaOH/KOH solution (75 mL) and water (275) were combined with the cooled reaction mixture. FIG. 4 shows an illustrative $^1$H NMR spectrum in $CD_3OD$ of the aromatic region of the titanium complex formed from 2 equivalents of catechol and 1 equivalent of 3,4-dihydroxybenzenesulfonic acid before addition of base. The resulting solution was filtered to remove excess solid, and a blood red solution having a pH of 12.61 was obtained. FIG. 5 shows an illustrative $^1$H NMR spectrum in $D_2O$ of the aromatic region of the titanium complex formed from 2 equivalents of catechol and 1 equivalent of 3,4-dihydroxybenzenesulfonic acid after addition of base. Other than having sharper peak shapes, the $^1$H NMR spectrum of the complex was largely similar to that of the coordination complex formed with intermediate purification of the 3,4-dihydroxybenzenesulfonic acid (see FIG. 2).

Although the disclosure has been described with reference to the disclosed embodiments, those skilled in the art will readily appreciate that these are only illustrative of the disclosure. It should be understood that various modifications can be made without departing from the spirit of the disclosure. The disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description.

What is claimed is the following:

1. A method comprising:
    heating a neat mixture of catechol and a sub-stoichiometric amount of sulfuric acid relative to the catechol to form a reaction product comprising a mixture of catechol and a monosulfonated catechol or a salt thereof; and
    without separating the catechol and the monosulfonated catechol or the salt thereof from one another, forming a coordination complex from the reaction product having a metal center with at least one unsubstituted catecholate ligand and at least one monosulfonated catecholate ligand bound thereto.

2. The method of claim 1, wherein the monosulfonated catechol is 3,4-dihydroxybenzenesulfonic acid.

3. The method of claim 1, wherein the neat mixture comprises up to about 0.7 stoichiometric equivalents of sulfuric acid relative to catechol.

4. The method of claim 3, wherein the neat mixture comprises between about 0.1 stoichiometric equivalents and about 0.7 stoichiometric equivalents of sulfuric acid relative to catechol.

5. The method of claim 3, wherein the neat mixture comprises between about 0.3 stoichiometric equivalents and about 0.5 stoichiometric equivalents of sulfuric acid relative to catechol.

6. The method of claim 1, wherein the neat mixture is heated at a temperature in a range from about 80° C. to about 130° C.

7. The method of claim 1, wherein the metal center is a transition metal.

8. The method of claim 7, wherein the transition metal is titanium and the coordination complex has a formula of:

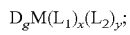

wherein:
    D is a counterion that is $H^+$, $NH_4^+$, $Na^+$, $K^+$, or any combination thereof;
    g is 2, 3, 4, 5, or mil 6;
    $L_1$ is the at least one unsubstituted catecholate ligand;
    $L_2$ is the at least one monosulfonated catecholate ligand; and
    x and y are non-zero numbers such that x+y=3.

9. The method of claim 8, wherein the coordination complex comprises both $Na^+$ and $K^+$ counterions.

10. The method of claim 1, further comprising:
    combining at least one aqueous base with the coordination complex; and
    obtaining an aqueous solution of the coordination complex.

11. The method of claim 10, wherein the coordination complex comprises both $Na^+$ and $K^+$ counterions.

12. The method of claim 10, wherein the metal center is titanium.

13. The method of claim 1, further comprising:
    combining an organic solvent with the reaction product before forming the coordination complex.

14. The method of claim 1, wherein the reaction product and the coordination complex are formed consecutively in a single reaction vessel.

15. A method comprising:
    heating a neat mixture of catechol and up to about 0.7 stoichiometric equivalents of sulfuric acid relative to the catechol at a temperature of about 80° C. or above to form a reaction product comprising a mixture of catechol and a monosulfonated catechol or a salt thereof, wherein the monosulfonated catechol is 3,4-dihydroxybenzenesulfonic acid;
    without separating the catechol and the monosulfonated catechol or the salt thereof from one another, forming a coordination complex from the reaction product having a metal center with at least one unsubstituted catecholate ligand and at least one monosulfonated catecholate ligand bound thereto;
    combining an aqueous base with the coordination complex to provide an aqueous solution of the coordination complex.

16. The method of claim 15, wherein the neat mixture comprises between about 0.1 stoichiometric equivalents and about 0.7 stoichiometric equivalents of sulfuric acid relative to catechol.

17. The method of claim 15, wherein the neat mixture comprises between about 0.3 stoichiometric equivalents and about 0.5 stoichiometric equivalents of sulfuric acid relative to catechol.

18. The method of claim 15, wherein the neat mixture is heated at a temperature in a range of from about 80° C. to about 130° C.

19. The method of claim 15, wherein the metal center comprises a transition metal.

20. The method of claim 19, wherein the transition metal is titanium and the coordination complex has a formula of:

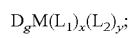

wherein:
    D is a counterion that is $NH_4^+$, $Li^+$, $Na^+$, $K^+$, or any combination thereof;
    g is 2, 3, 4, 5, or 6;
    $L_1$ is the at least one unsubstituted catecholate ligand;
    $L_2$ is the at least one monosulfonated catecholate ligand; and
    x and y are non-zero numbers such that x+y=3.

21. The method of claim 20, wherein the coordination complex comprises both $Na^+$ and $K^+$ counterions.

22. The method of claim 15, further comprising:
    adding an organic solvent to the reaction product before forming the coordination complex.

* * * * *

UNITED STATES PATENT AND TRADEMARK OFFICE
CERTIFICATE OF CORRECTION

PATENT NO. : 10,316,047 B2
APPLICATION NO. : 15/060495
DATED : June 11, 2019
INVENTOR(S) : Humbarger et al.

It is certified that error appears in the above-identified patent and that said Letters Patent is hereby corrected as shown below:

Item [56], References Cited, U.S. Patent Documents, replace:
Page 2, Column 2, Line 33 "Frost" with --Frost et al.--

Item [56], References Cited, OTHER PUBLICATIONS, replace:

Page 3, Column 2, Line 17 "Davies, "Electroceramics from Source Materials via Molecular Intermediates: BaTI0$_3$ from TI0$_2$ via [TI(catecholate)$_3$]$^{2-}$," May 1990 J. Am. Cerarn. Soc., Aug. 1990, 73(5), 1429-30." with --Davies, "Electroceramics from Source Materials via Molecular Intermediates: BaTiO$_3$ from TiO$_2$ via [Ti(catecholate)$_3$]$^{2-}$," Journal of the American Ceramics Society, May. 1990, 73(5), 1429-30--

Page 3, Column 2, Line 41 "S. Saito, et al. "DPPH radical-scavenging reaction of protocatechuic acid: difference in reactivity between adds and their esters," Helv. Chim. Acta, 2006, pp. 1395-1407, 89." with --S. Saito, et al. "DPPH radical-scavenging reaction of protocatechuic acid: difference in reactivity between acids and their esters," Helv. Chim. Acta, 2006, pp. 1395-1407, 89.--

Page 4, Column 1, Line 20 "Davies, "Electroceramics from Source Materials via Molecular Intermediates: PbTi03 from Ti02 via [Ti(catecholate)3]2$^-$," J. Am. Ceram. Soc., Aug. 1990, 73(8), 2570-2572," with --Davies, "Electroceramics from Source Materials via Molecular Intermediates: PbTiO$_3$ from TiO$_2$ via [Ti(catecholate)$_3$]$^{2-}$," Journal of the American Ceramics Society, Aug. 1990, 73(8), 2570-2572.--

Page 4, Column 1, Line 34 "Kim, "Novel catalytic effects of Mn304 for all vanadium redox flow batteries," Chem. Commun., Apr. 2012, 48(44), 5455-5457." with --Kim, "Novel catalytic effects of Mn$_3$O$_4$ for all vanadium redox flow batteries," Chem. Commun., Apr. 2012, 48(44), 5455-5457.--

Page 4, Column 2, Line 18 "Raymond , "Coordination isomers of biological iron transport compounds. VI. Models of the enterobactin coordination site. A crystal field effect in the structure of potassium tris(catecholato )chromate( III) and -ferrate( III) sesq u ihyd rates, K3[M( 02C6H4 )3]. 1 . 5H$_2$0, M=chromium, iron," J. Am. Chem. Soc., Mar. 1976, 98(7), 1767-1774." with --Raymond, Signed and Sealed this
Twenty-sixth Day of November, 2019

Andrei Iancu
*Director of the United States Patent and Trademark Office*

"Coordination isomers of biological iron transport compounds. VI. Models of the enterobactin coordination site. A crystal field effect in the structure of potassium tris(catecholato)chromate(III) and -ferrate(III) sesquihydrates, $K_3[M(O_2C_6H_4)_3] \cdot 1.5H_2O$, M = Cr, Fe$^1$," J. Am. Chem. Soc., Mar. 1976, 98(7), 1767-1774.--

In Claim 8, Column no. 25, Line no. 45 replace:
"D is a counterion that is H+, NH$_4$+,Na+, K+, or any" with --D is a counterion that is H+, NH$_4$+, Li+, Na+, K+, or any--

In Claim 8, Column no. 25, Line no. 47 replace:
"g is 2, 3, 4, 5, or mil 6;" with --g is 2, 3, 4, 5, or 6;--

In Claim 20, Column no, 25, Line no. 42 replace:
"$D_gM(L_1) \times (L_2)_y$;" with --$D_gTi(L_1) \times (L_2)_y$;"--